Figure 1:
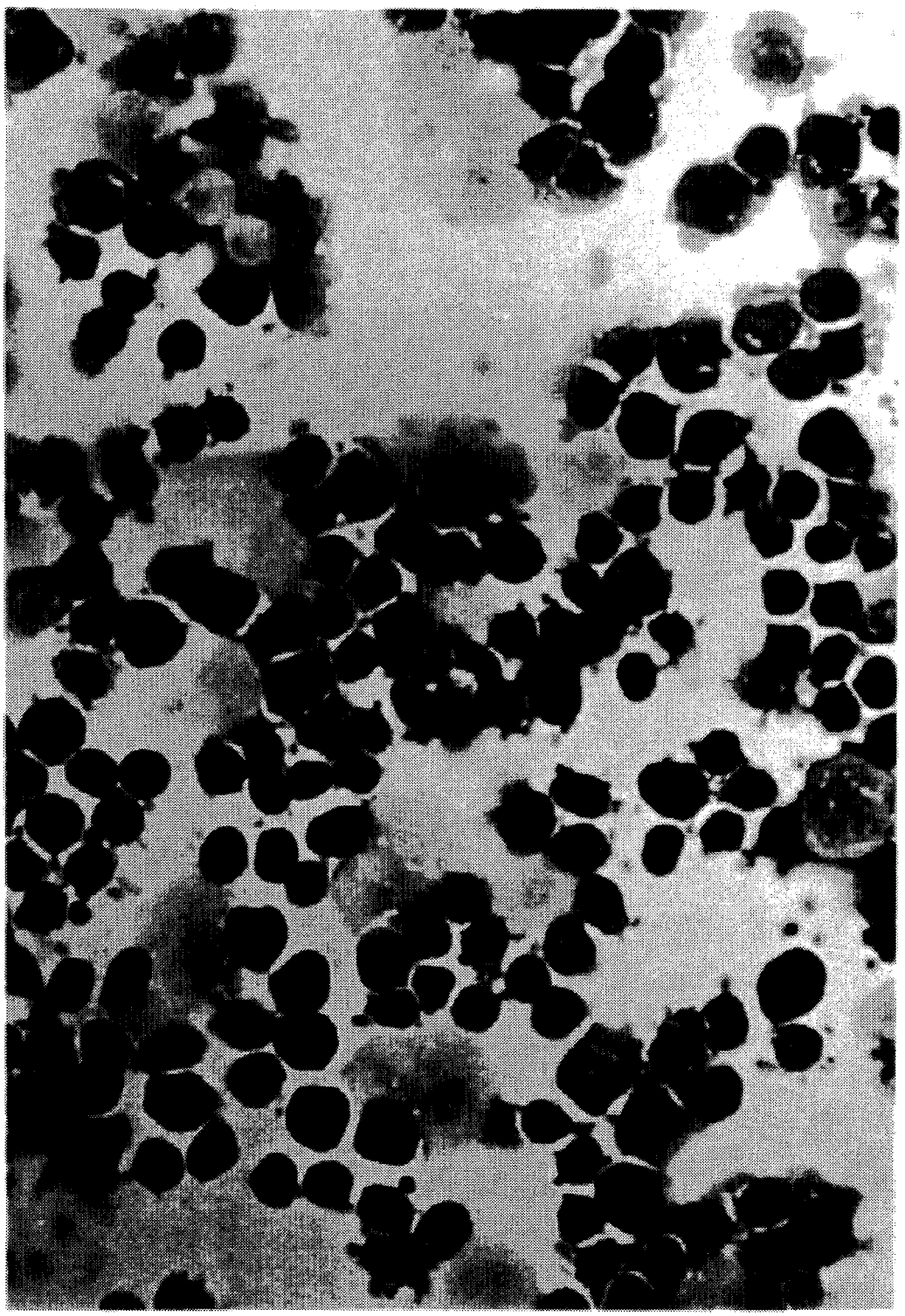

United States Patent [19]

Naughton et al.

[11] Patent Number: 5,559,022
[45] Date of Patent: Sep. 24, 1996

[54] LIVER RESERVE CELLS

[75] Inventors: Brian A. Naughton, El Cajon; Benson Sibanda, Oceanside, both of Calif.

[73] Assignee: Advanced Tissue Sciences, Inc., La Jolla, Calif.

[21] Appl. No.: 378,762

[22] Filed: Jan. 26, 1995

Related U.S. Application Data

[63] Continuation of Ser. No. 958,621, Oct. 9, 1992, abandoned.
[51] Int. Cl.$^6$ .............................. C12N 5/06; C12N 5/08
[52] U.S. Cl. .................................. 435/240.2; 435/240.1; 424/93.1
[58] Field of Search .............................. 424/93.21, 9.2, 424/93.1; 435/240.2, 172.3, 240.1; 935/70, 71

[56] References Cited

PUBLICATIONS

S. Sell Cancer Research, vol. 50 (1 Jul. '90) pp. 3811–3815.
Y. Bujanover et al. (Abstract) Hepatology (Baltimore) vol. 8 #4 ('88) pp. 722–727.
P. Sudhakavan et al. (Abtsract) Exp. Cell Res., vol. 167 #2 ('86) pp. 505–516.
J. Sidhu et al. (Abstract) In Vitro Toxicology, vol. 7 #3 ('94) pp. 225–242.
J. Chowdhury et al. Science, vol. 254 (20 Dec. '91) pp. 1802–1805.
A. Demetriou et al. Science, vol. 233 (12 Sep. '86) pp. 1190–1192.
T. Lapidot et al. Science, vol. 255 (28 Feb. '92) pp. 1137–1141.
C. Petropoulos et al. Cancer Research, vol. 45 (Nov. '85) pp. 5762–5768.
J. Gumucio et al. Hepatology, vol. 6, #5 ('86) pp. 932–944.
S. Sigal. Am. J. Physiology, vol. 263, ('92) pp. GG139–148.
J. Wilson et al. PNAS, vol. 87 (Nov. '90) pp. 8437–8441.
R. Weiss, "Getting New Genes" The Washington Post Health Section, (15 Feb. '94) pp. 11–16.
Sell, Cancer Res., vol. 50 ('90) pp. 3811–3815.
Harrison et al. Expil. Hematology, vol. 21 ('93) pp. 206–219.
Lapidot et al. Science, vol. 255 (1992) pp. 1137–1141.
Huang et al. Nature, vol. 360 (1992) pp. 745–749.
Gumucio et al. (Abstract) Hepatology, vol. 6 (#5) (1986) pp. 932–944.
Chowdhury et al. Science, vol. 254 (1991) pp. 1802–1805.
Wilson et al. P.N.A.S., vol. 87 (1990) pp. 8437–8441.
Demetriov et al. Science, vol. 233 (1986) pp. 1190–1192.
Petropoulos et al. Cancer Res., vol. 45 (1985) pp. 5762–5768.

*Primary Examiner*—Charles Rories
*Attorney, Agent, or Firm*—Pennie & Edmonds

[57] ABSTRACT

The present invention relates to liver reserve or progenitor cells. In particular, it relates to the isolation, characterization, culturing, and uses of liver reserve cells. Liver reserve cells isolated by density gradient centrifugation can be distinguished from other liver parenchymal cells by their morphology, staining characteristics, high proliferative activity and ability to differentiate in vitro. In long-term cultures described herein, these cells expand in numbers and differentiate into morphologically mature liver parenchymal cells, capable of mediating liver-specific functions. Therefore, isolated liver reserve cells may have a wide range of applications, including, but not limited to, their uses as vehicles of exogenous genes in gene therapy, and/or to replace and reconstitute a destroyed, infected, or genetically deficient mammalian liver by transplantation.

11 Claims, 18 Drawing Sheets

Ethoxyfluorescein ethyl ester → Fluorescein

- Freshly Isolated Liver Cells
- 24 hr Suspension Culture
- 17 day Co-culture
- 26 day Co-culture
- 41 day Co-culture
- 58 day Co-culture

LIVER RESERVE CELLS

This is a continuation of application Ser. No. 07/958,621, filed Oct. 9, 1992, now abandoned.

1. INTRODUCTION

The present invention relates to liver reserve or progenitor cells. In particular, it relates to the isolation, characterization, culturing, and uses of liver reserve cells. Liver reserve cells isolated by density gradient centrifugation can be distinguished from other liver parenchymal cells by their morphology, staining characteristics, high proliferative activity and ability to differentiate in vitro. In long-term cultures described herein, these cells expand in numbers and differentiate into morphologically mature liver parenchymal cells, capable of mediating liver-specific functions. Therefore, isolated liver reserve cells may have a wide range of applications, including, but not limited to, their use as vehicles of exogenous genes in gene therapy, and/or to replace and reconstitute a destroyed, infected, or genetically deficient mammalian liver by transplantation.

2. BACKGROUND OF THE INVENTION

The liver is a dynamic organ that plays an important role in a variety of physiological processes. The complex functions of the liver include metabolism, storage, excretion, secretion of plasma proteins such as albumin and detoxification of harmful substances by enzymes of the cytochrome P-450 system. In addition, the usually quiescent liver is also capable of remarkable mitotic activities under certain circumstances.

2.1. LIVER CELLS

The major cell population of the liver is the parenchymal cells (PC), also known as hepatocytes. The liver also contains several other cell types such as endothelial cells, adipocytes, fibroblastic cells and Kupffer cells, collectively referred to as stromal (littoral) cells. The ability of liver cells to undergo rapid regeneration, when the liver is damaged or partially removed, has led to speculation for the existence of a population of stem cells or reserve cells, capable of self-renewal and differentiation. However, prior to the present invention, such liver reserve cells had never been identified or their characteristics described.

"Oval" cells have been described in the adult mammalian liver. These cells have a high nuclear to cytoplasmic size ratio, are approximately 40% of the diameter of freshly isolated PC, express enzyme activities consistent with those of fetal hepatocytes, and have a relatively high proliferation rate (Tsao et al., 1984, Exp. Cell Res. 154:38–52; Farber et al., 1956, Cancer Res. 16:142–149). However, animals usually must be treated in vivo with ethionine, 2-acetylaminofluorene, or other carcinogens to generate these cells. Some investigators have hypothesized that oval cells may be a manifestation of PC retrodifferentiation (Grisham, 1980, Ann. N.Y. Acad. Sci. 349:128–137; Firminger, 1955, J. Nat. Cancer Instit. 15:1427–1441) but they may resemble endothelial cells more closely (Fausto et al., 1987, In: Cell Separation: Methods and selected applications, Vol. 4, T. G. Pretlow II and T. P. Pretlow, editors, Academic Press, London, pp 45–78). The role of oval cells as putative stem cells or reserve cells has never been established, and it has been the subject of a number of investigations (Fausto et al., 1987, In: Cell Separation: Methods and selected applications, Vol. 4, T. G. Pretlow II and T. P. Pretlow, editors, Academic Press, London, pp 45–78).

2.2. LIVER CULTURES

In an attempt to study the diverse liver functions and the cell types responsible therefor, in vitro cultures of liver cells have been prepared from humans as well as from experimental animals. Primary cultures of rat hepatocytes have been used extensively to study the effects of potential toxins on enzyme leakage, metabolism, and cellular membranes (Grisham, 1979, Int. Rev. Exp. Pathol. 20:123–210; Acosta and Mitchell, 1981, Biochem. Pharmacol. 30:3225–3230). However, such culture systems have a number of drawbacks, and none have provided for the proliferation of liver PC or the identification of liver reserve cells.

In vitro, adult hepatocytes proliferate for only short time periods, although their ability to produce albumin and display cytochrome P-450 enzyme activity may be prolonged if they are co-cultured with other liver-derived extracellular matrix substances or with certain combinations thereof. In liquid culture, the viability of hepatocytes and the ability of these cells to manifest inducible cytochrome P-450 enzyme activity decline as a function of time (Sirica and Pitot, 1980, Pharmacol. Rev. 31:205–228). In addition, cell division usually is limited to the first 24–48 hr of culture (Clayton and Darnell, 1983, Mol. Cell. Biol. 3:1552–1561; Chapman et al., 1973, J. Cell Biol. 59:735–747). The viability of adherent hepatocytes in monolayer cultures persists for somewhat longer periods but specialized activity is also lost rapidly (Deschenes et al., 1980, In Vitro 16:722–730).

Towards the goal of enhancing hepatocyte growth and prolonging liver-specific functions in vitro, hepatic cells have been cultured on various matrices including type I collagen plates and membranes (Michalopoulos and Pitot, 1975, Exp. Cell Res. 94:70–78), homogenized liver biomatrix (Reid et al., 1980, Ann. N.Y. Acad. Sci. 349:70–76), in collagen type IV or laminin-rich gels (Bissell et al., 1987, J. Clin. Invest. 79:801–812), sandwiched between two layers of type I collagen (Dunn et al., 1989, FASEB J. 3:174–177), and on plates coated with fibronectin or the other extracellular matrix proteins (Deschenes et al., 1980, In Vitro 16:722–730). All of these methods have been reported to extend the functional life of hepatocytes in vitro to some extent.

Substantial improvements in this regard were produced by culturing PC with various types of non-parenchymal stromal or littoral hepatic cells or non-hepatic stromal cells. Both human and rat hepatocytes which were co-cultured with liver endothelial cells of the same species maintained specific functions for weeks in culture, although they did not undergo a significant expansion in numbers (Guguen-Guilluozo, et al., 1983, Exp. Cell Res. 143:47–54; Begue et al., 1983, Biochem. Pharmacol. 32:1643–1646). Rat hepatocytes which were co-cultured with human fibroblasts (Kuri-Harcuch and Mendoza-Figueroa, 1989, Differentiation 41:148–157) and endothelial cells (Begue et al., 1983, Biochem. Pharmacol. 32:1643–1646) were reported to sustain cytochrome P-450 activity for more than 10 days. Thus, these mixed hepatocyte co-culture systems may provide microenvironments similar to those in vivo by optimizing cell-cell interactions. In addition, various PC functions may be regulated and/or optimized by other hepatic cells. For example, Kupffer cell secretory products have been reported to modulate PC cytochrome P-450 enzyme activity (Peterson and Renton, 1984, J. Pharmacol. Exp. Ther.

229:299–304). The attachment of PC to fibroblasts is evidently contingent upon the secretion of specialized extracellular matrix substances by Kupffer cells (Michalopoulos et al., 1979, In Vitro 15:769–806). Hepatic endothelial cells also may produce important components of the extracellular matrix (Guguen-Guilluozo, et al., 1983, Exp. Cell Res. 143:47–54), and adipocytes may provide the requisite raw materials for the renewal of cell membranes in metabolically-active hepatocytes.

Although the viability and functional activities of cultured hepatic PC can be prolonged in vitro if the cells are co-cultured with non-parenchymal liver stromal cells, support cells from other tissues, or their secretory products, PC proliferation is limited or absent in these systems. Mitoses in co-cultures of hepatic cells have been ascribed primarily to non-parenchymal elements (Guguen-Guilluozo, et al., 1983, Exp. Cell Res. 143:47–54). Several reports indicate that non-parenchymal liver cells may express functions similar to hepatocytes (Grisham, 1980, Ann. N.Y. Acad. Sci. 349:128–137) although the nature of these non-PC has not been unequivocally established.

The growth of rat hepatocytes has been particularly enhanced when cultured on a three-dimensional template consisting of hepatic-derived stromal cells attached to a nylon filtration screen (Naughton and Naughton, 1991, U.S. Pat. No. 5,032,508). The stromal compartment contains all of the adherent cells found in liver tissues including Kupffer cells, vascular and bile duct endothelial cells, fibroblasts, and some adipocyte-like cells. These cells elaborate a matrix similar in some respects to that observed in liver in vivo and support long-term growth of PC and their liver specific functions in vitro. However, prior to the present invention, the existence of liver reserve cells in such cultures had never been established.

3. SUMMARY OF THE INVENTION

The present invention relates to liver reserve cells, a method of isolating and culturing liver reserve cells, and a method of using the liver reserve cells with or without exogenous genetic materials in transplantation or implantation into an individual with a specific liver disorder.

The invention is based, in part, on Applicants' discovery that rat liver PC can be grown in a culture system to sustain liver-specific functions for over 60 days, and the culture contains all of the cell types found in the liver in vivo. The co-cultures composed of liver PC grown upon liver stromal cells which have attached to a nylon screen, when placed in liquid medium, become suspended between the bottom of the flask and the surface of the medium, enhancing the three-dimensional growth effect. Hepatocellular DNA synthesis, which persists for >7 weeks in vitro, is enhanced by supplementing the medium with saturated transferrin and/or conditioning the medium with sera derived from the hepatic veins of partially hepatectomized rats. Liver specific functions such as albumin synthesis and cytochrome P-450 enzyme activity are evident for as long as 60 days in culture. In addition, the expression of both class I MHC antigens on cultured hepatic parenchyma and MHC class II antigens on Kupffer cells declined as a function of time in vitro. Sections through pellets of adherent zone cells revealed normal parenchymal cell architecture.

In the course of isolating and culturing liver PC, a population of previously unknown large acidophilic hepatic cells, which have a higher proliferation rate than other hepatic cells, were isolated using density gradient centrifugation. These cultured acidophilic hepatocytes undergo cell division in the culture system described above, and cell cycle analysis suggests that they are PC rather than stromal cells because of their total DNA content. Medium containing transferrin saturated with ferric iron and supplemented with ferrous sulphate and ferric citrate and/or conditioned with sera from hepatectomized rats enhance the mitotic indices of inocula of either acidophilic cells alone or mixed acidophilic and mature PC on suspended nylon screen cultures. Most importantly, these acidophilic cells are able to develop into hepatocytes in culture and perform liver-specific functions, and thus, are believed to be liver reserve cells.

The invention is described by way of examples in which rat liver reserve cells are isolated and their cytologic and biologic properties characterized. A relatively homogeneous (>90%) population of liver reserve cells can be maintained in cultures, and shown to retain proliferative and differentiative capabilities. A wide variety of uses for the liver reserve cells are encompassed by the invention, described herein. In particular, the high proliferative rate of these cells allows them to be ideal recipients for stable insertion of exogenous genes in gene therapy of various liver disorders.

4. BRIEF DESCRIPTION OF THE DRAWINGS

FIG. 1. Photomicrograph of a cytosmear of the pellet of a 70% Percoll density centrifugation. Mature parenchymal cells stain darkly; the stain had to be applied for a longer time in order to visualize the larger, lightly staining acidophilic cells.

Figure 2:

FIG. 2. Photomicrograph of a cytosmear of acidophilic cells from the discontinuous "neat Percoll" procedure. Diff-Quik stain. Original magnification=1000X. These cells are 25–30% larger than other cells in the preparation, are vacuolated and faintly staining, display numerous, large nucleoli, and have a lower nuclear: cytoplasmic size ratio than other hepatic cells of the isolate.

Figure 3:
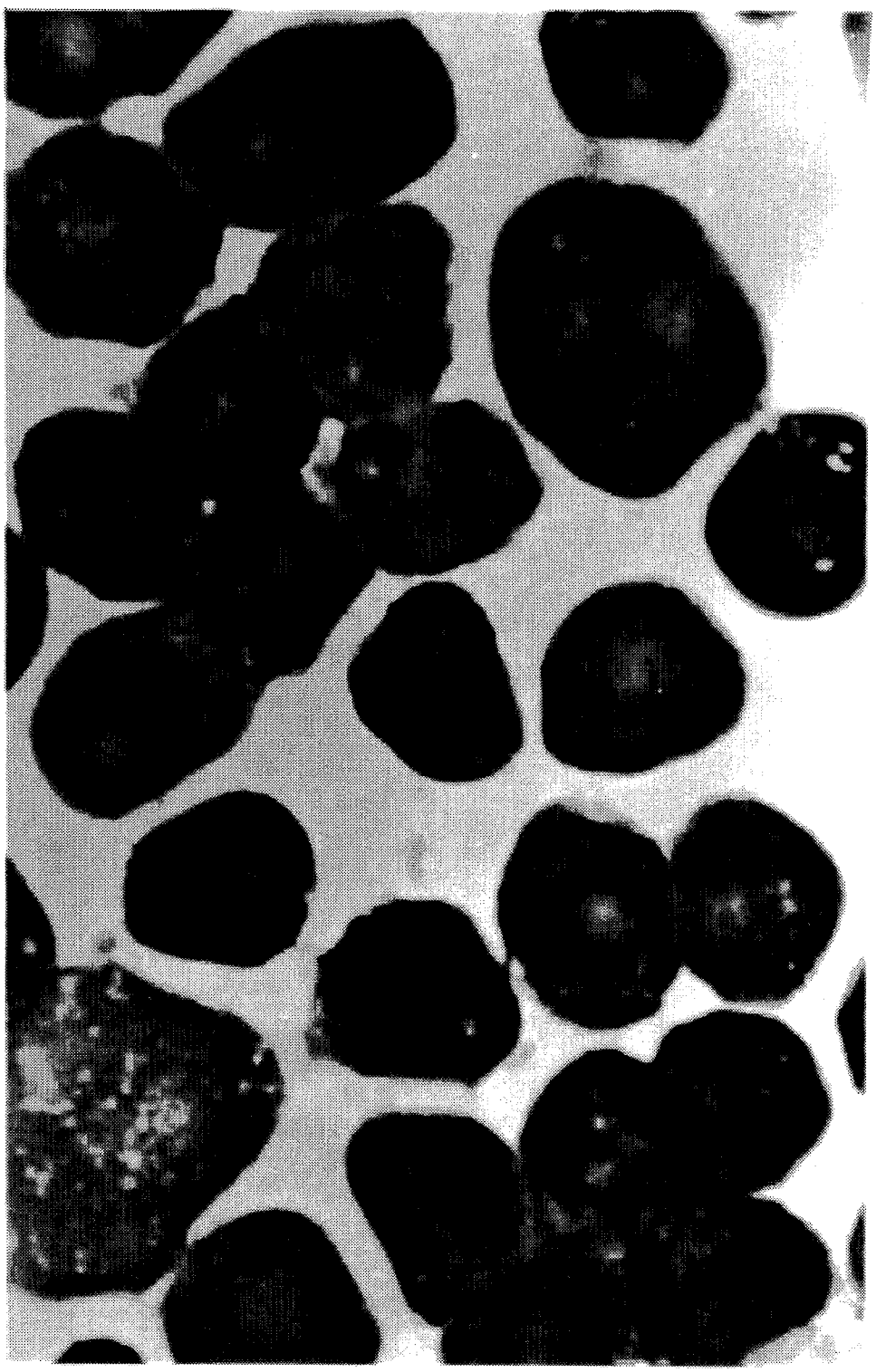

FIG. 3. Cytosmear of morphologically mature parenchymal cells in the non-adherent zone of monolayer cultures initiated with acidophilic cells (10 day culture).

Figure 4:
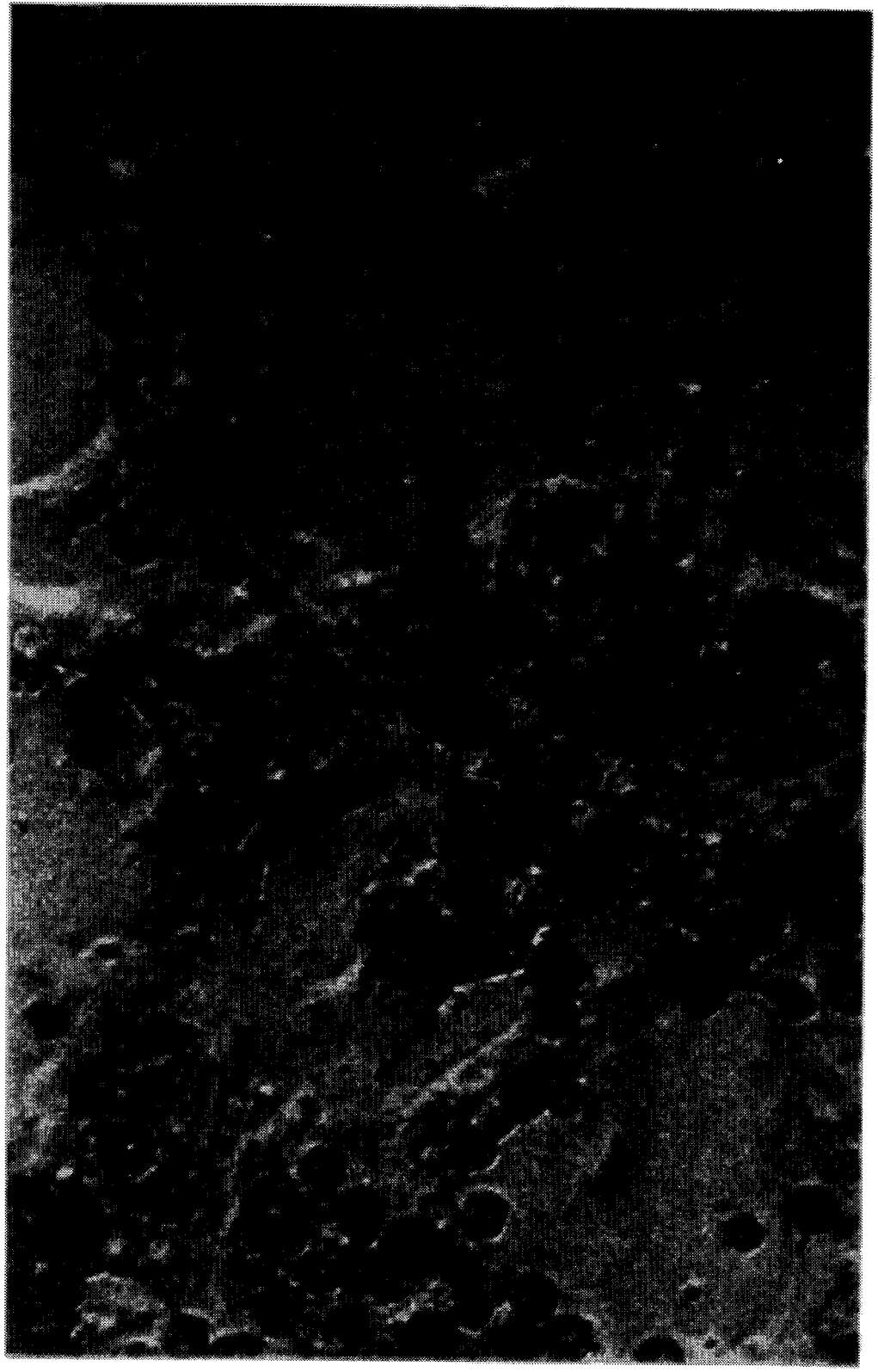

FIG. 4. Mature parenchymal cells adhering to and possibly emanating from an adherent zone of acidophilic cells in monolayer culture.

Figure 5A:
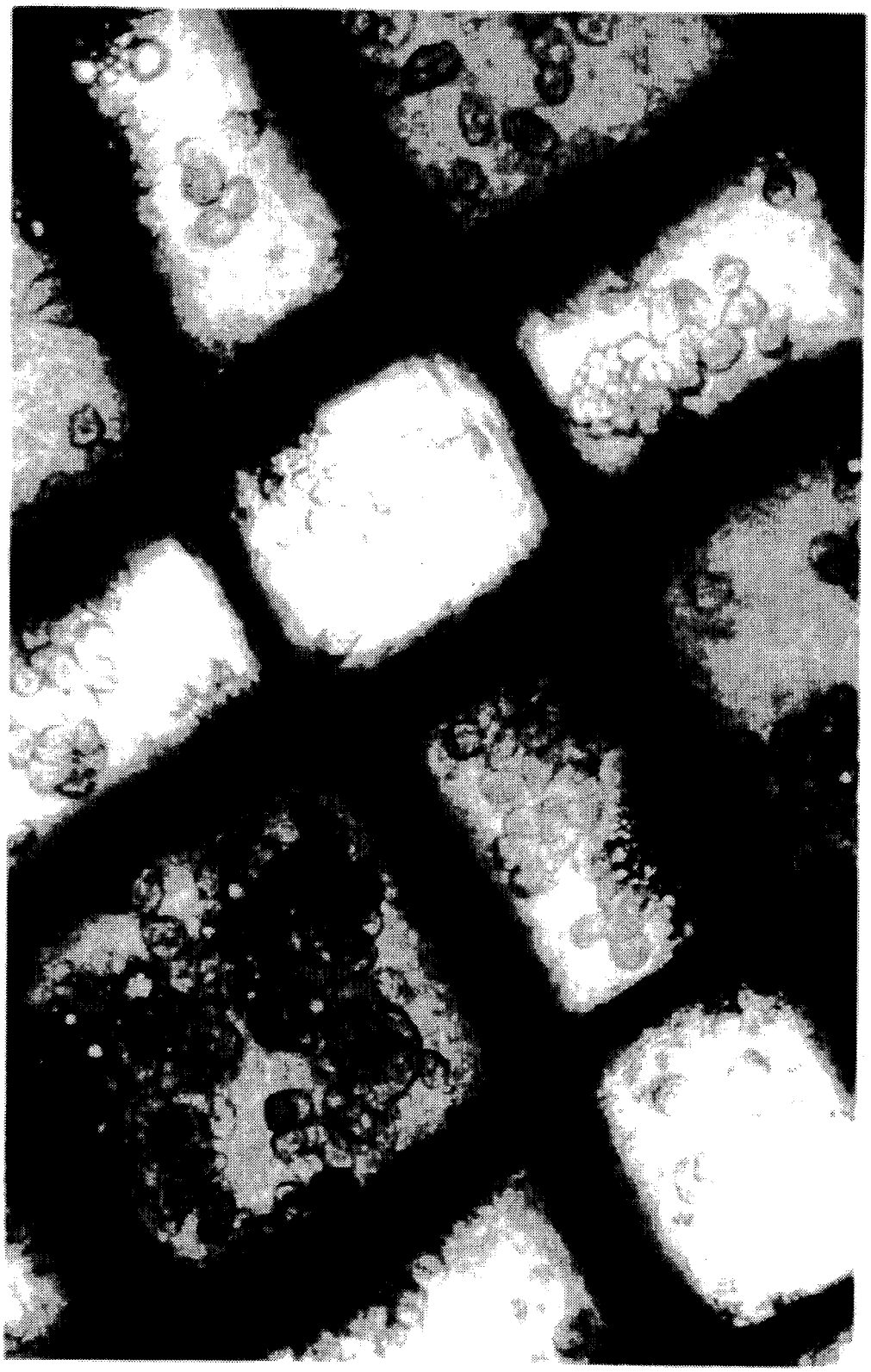
Figure 5B:

FIGS. 5A and 5B. FIG. 5A. Inverted phase micrograph of a liver co-culture established by inoculating cells from a 70% Percoll density gradient onto a sub-confluent layer of liver stromal cells on nylon screen.

FIG. 5B. Inverted phase micrograph of a liver co-culture established by inoculating acidophilic liver reserve cells isolated using a discontinuous Percoll density gradient procedure.

Figure 6:
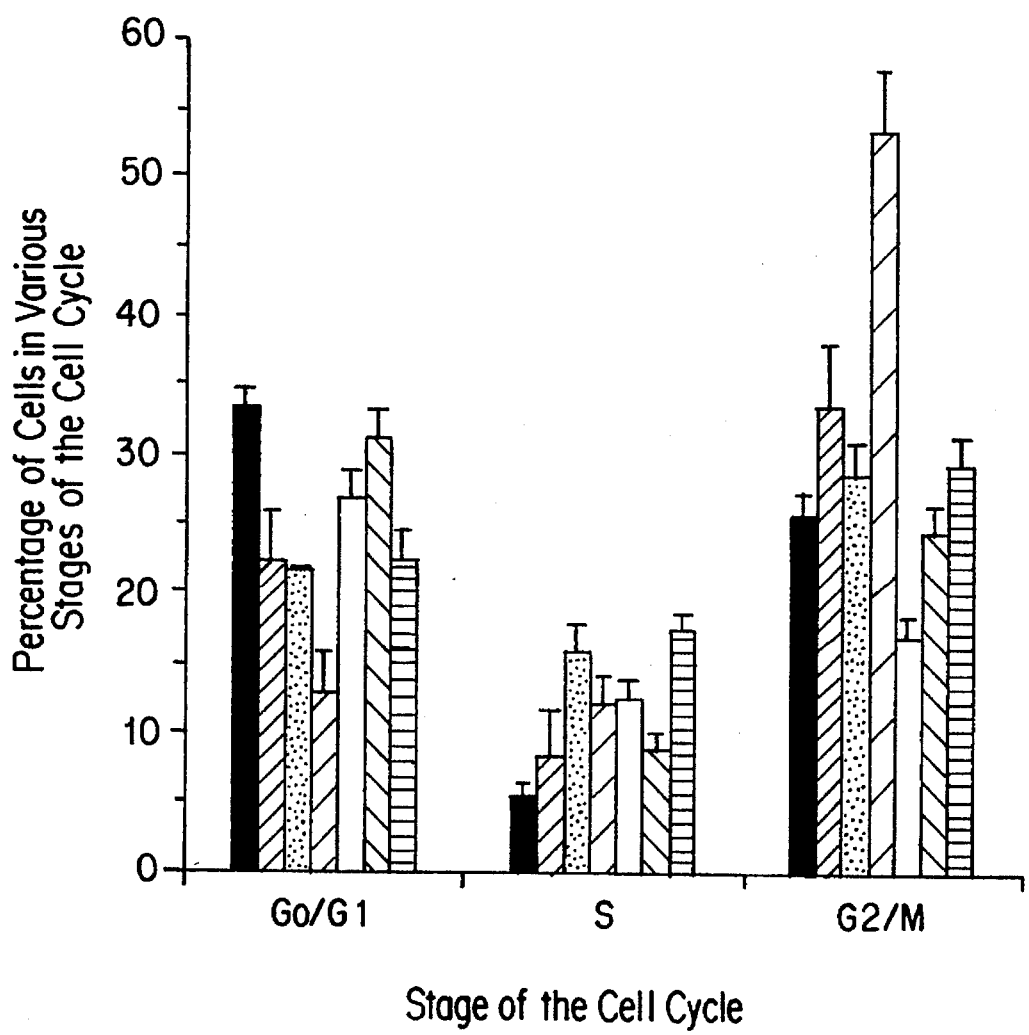

FIG. 6. Cell-cycle analysis of liver co-cultures under different conditions as measured in isolated nuclei stained with propidium iodide by flow cytometry.

Figure 7:
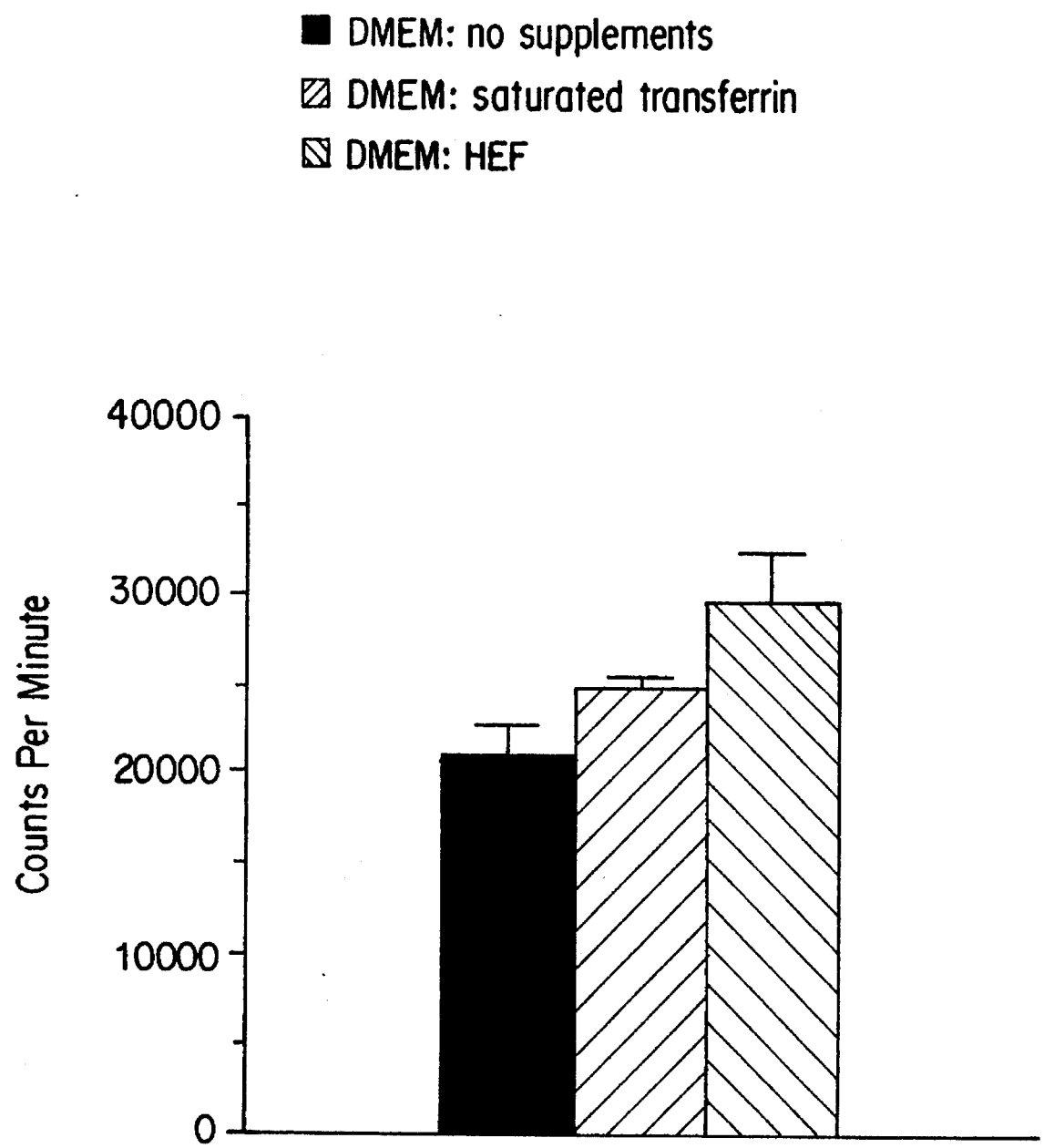

FIG. 7. Tritiated thymidine incorporation into liver cells under various culture conditions.

Figure 8:
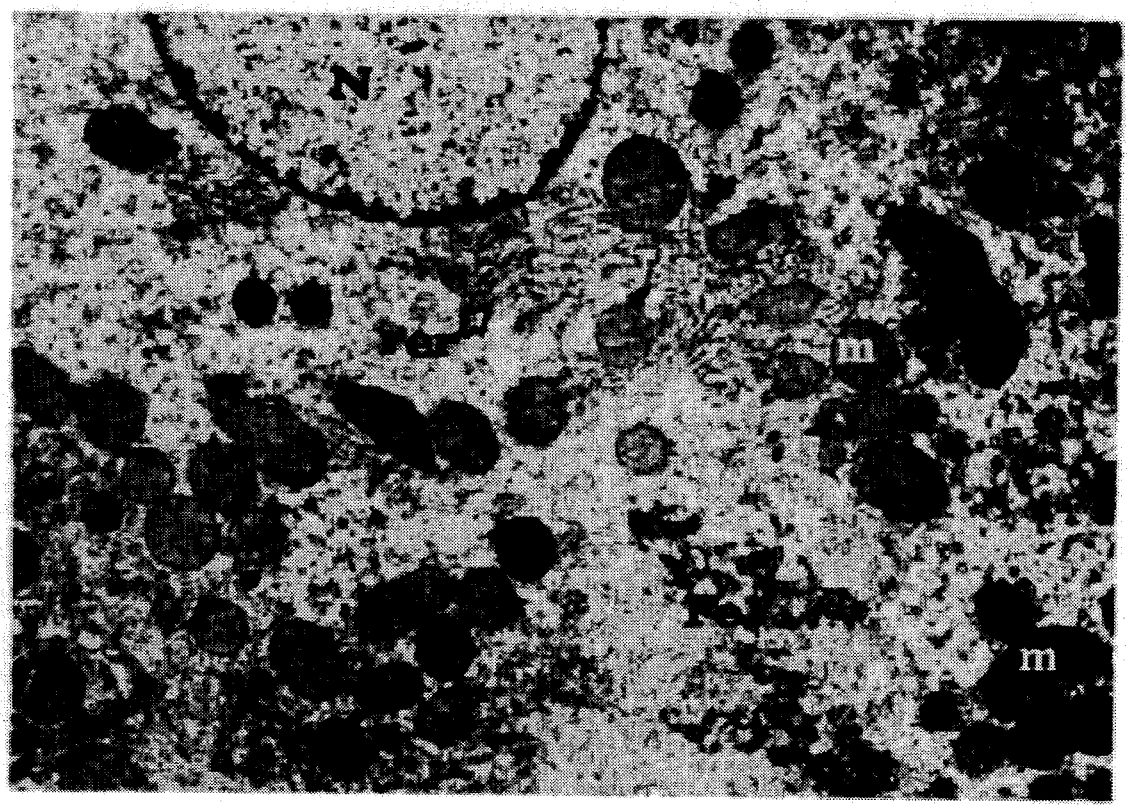

FIG. 8. Transmission electron micrograph of a section through a pellet of enzyme-dissociated adherent zone cells of a nylon screen liver cell culture 85 days after inoculation. Patent mitochondrial ultrastructure and metabolically active rough endoplasmic reticulum membranes are seen. Original magnification=2,800X.

Figure 9A:
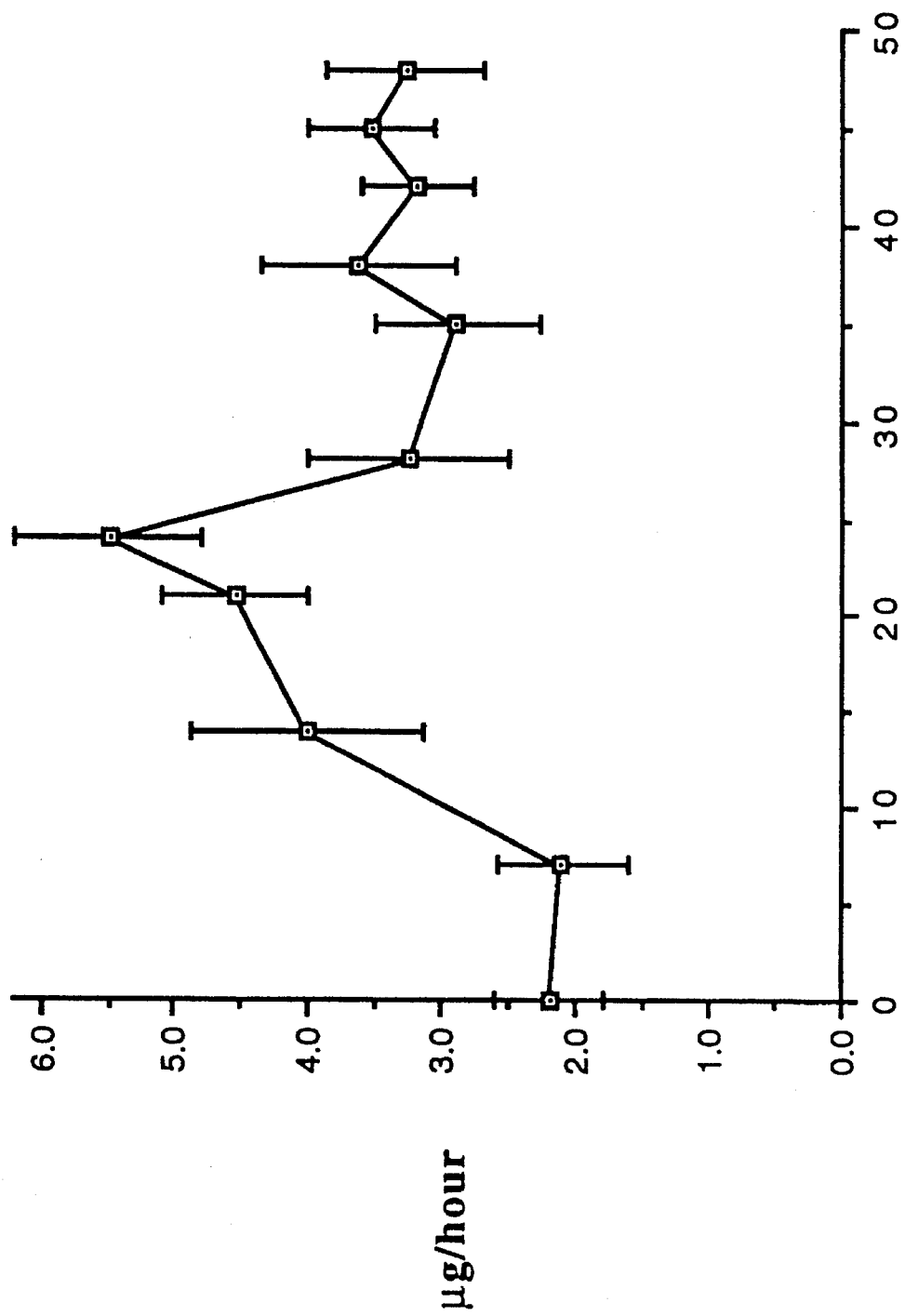
Figure 9B:
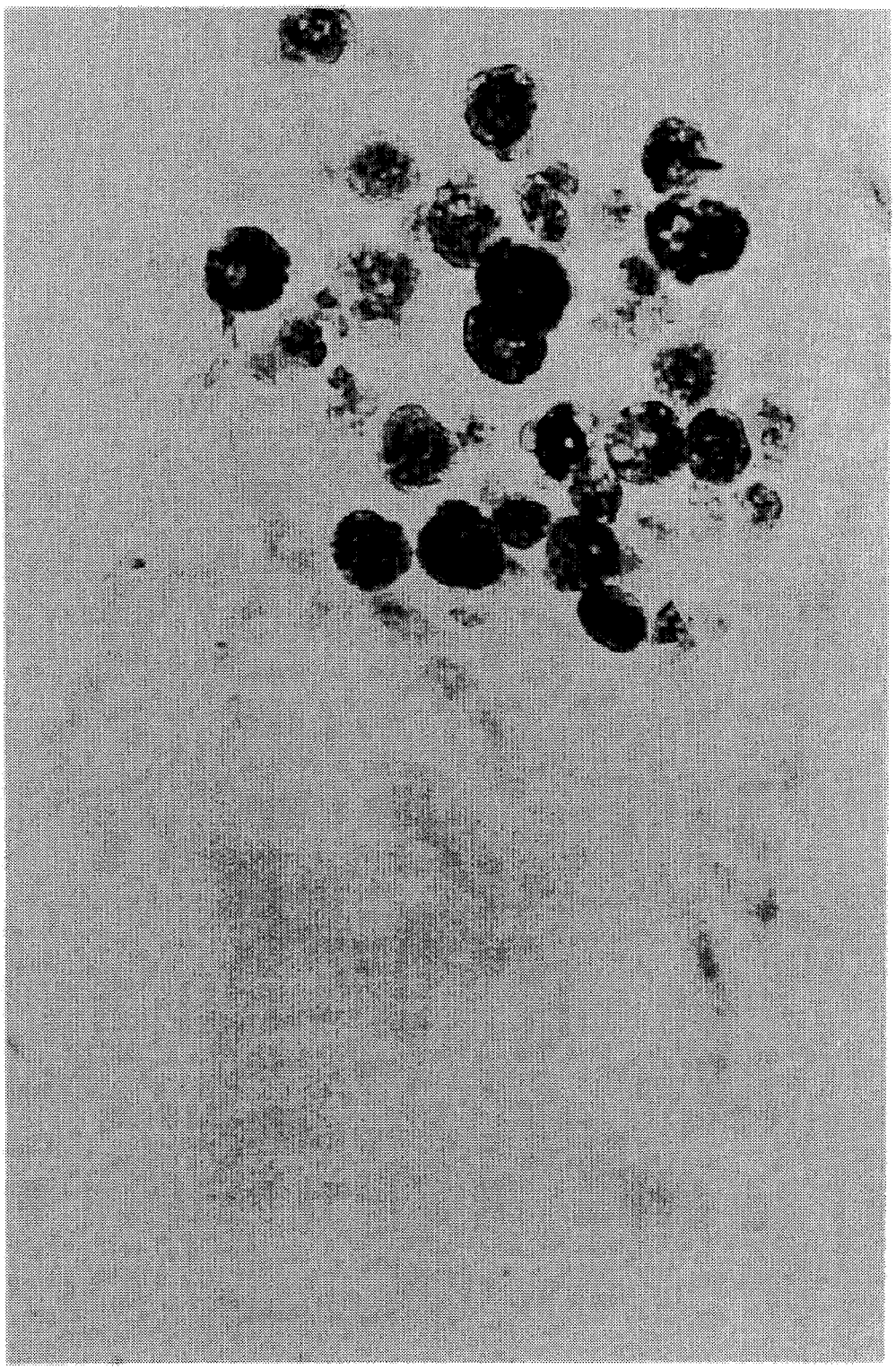

FIGS. 9A and 9B. FIG. 9A. Mean albumin secretion ($\pm 1$ standard error of the mean) into the medium by cells from the adherent zones of suspended nylon screen liver cultures of various ages.

FIG. 9B. Immunoperoxidase stain for albumin in a 40 day liver co-culture.

Figure 10A:
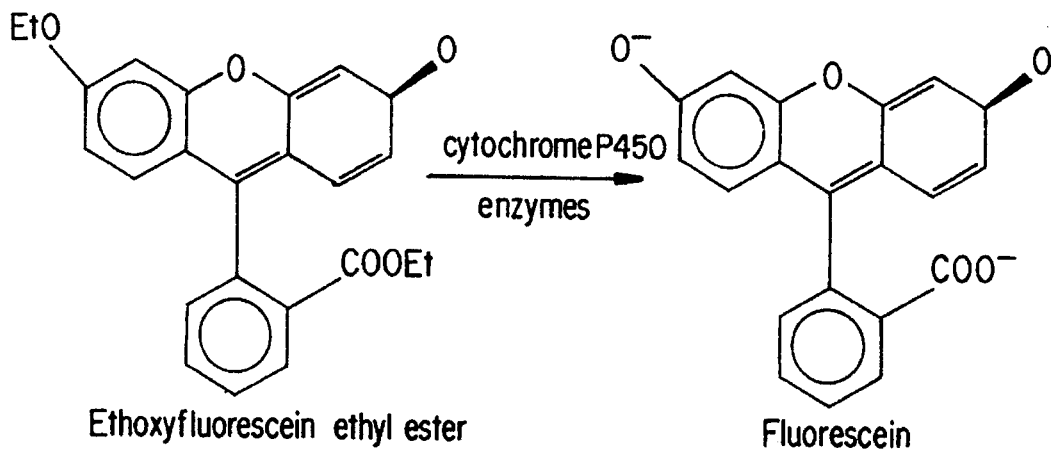
Figure 10B:
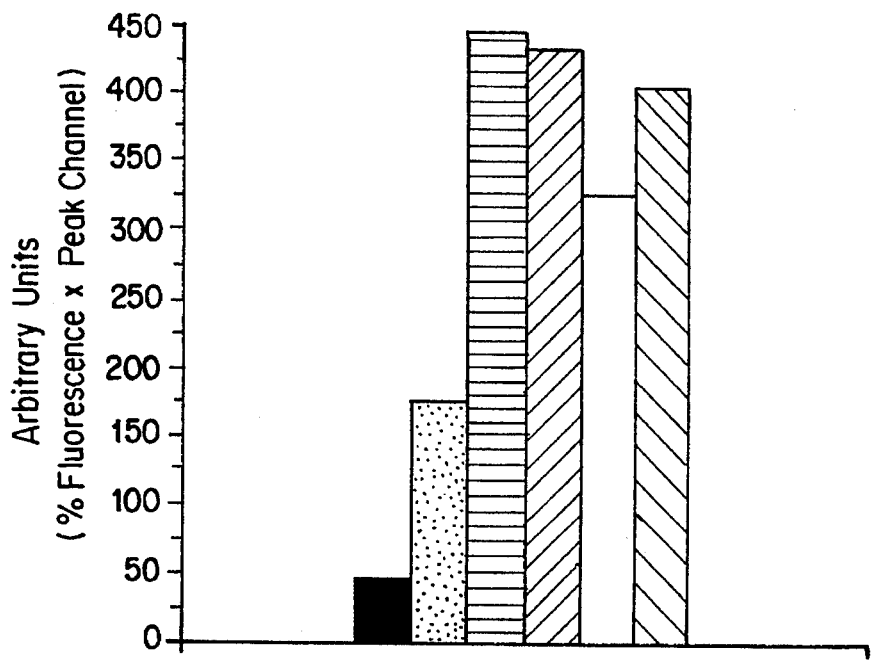

FIGS. 10A and 10B. Diagram of the metabolic conversion of ethoxyfluorescein ethyl ester (EFEE) to fluorescein(F) by cells with cytochrome P-450 enzyme activity (FIG. 10A). Cytochrome P-450 enzyme activity in liver cultures of various ages determined by EFEE to F conversion as measured by flow cytometry (FIG. 10B).

Figure 11A:
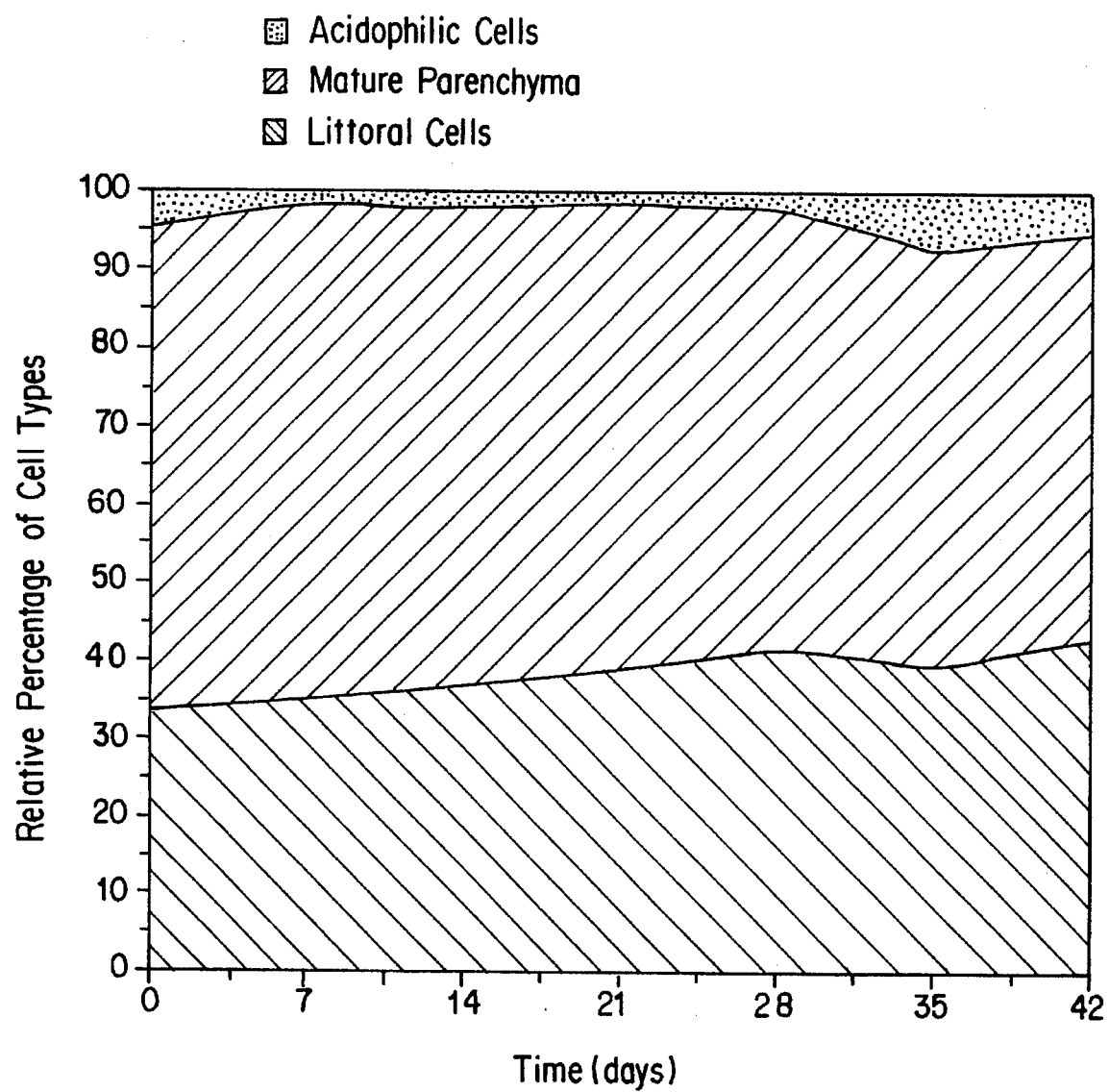
Figure 11B:
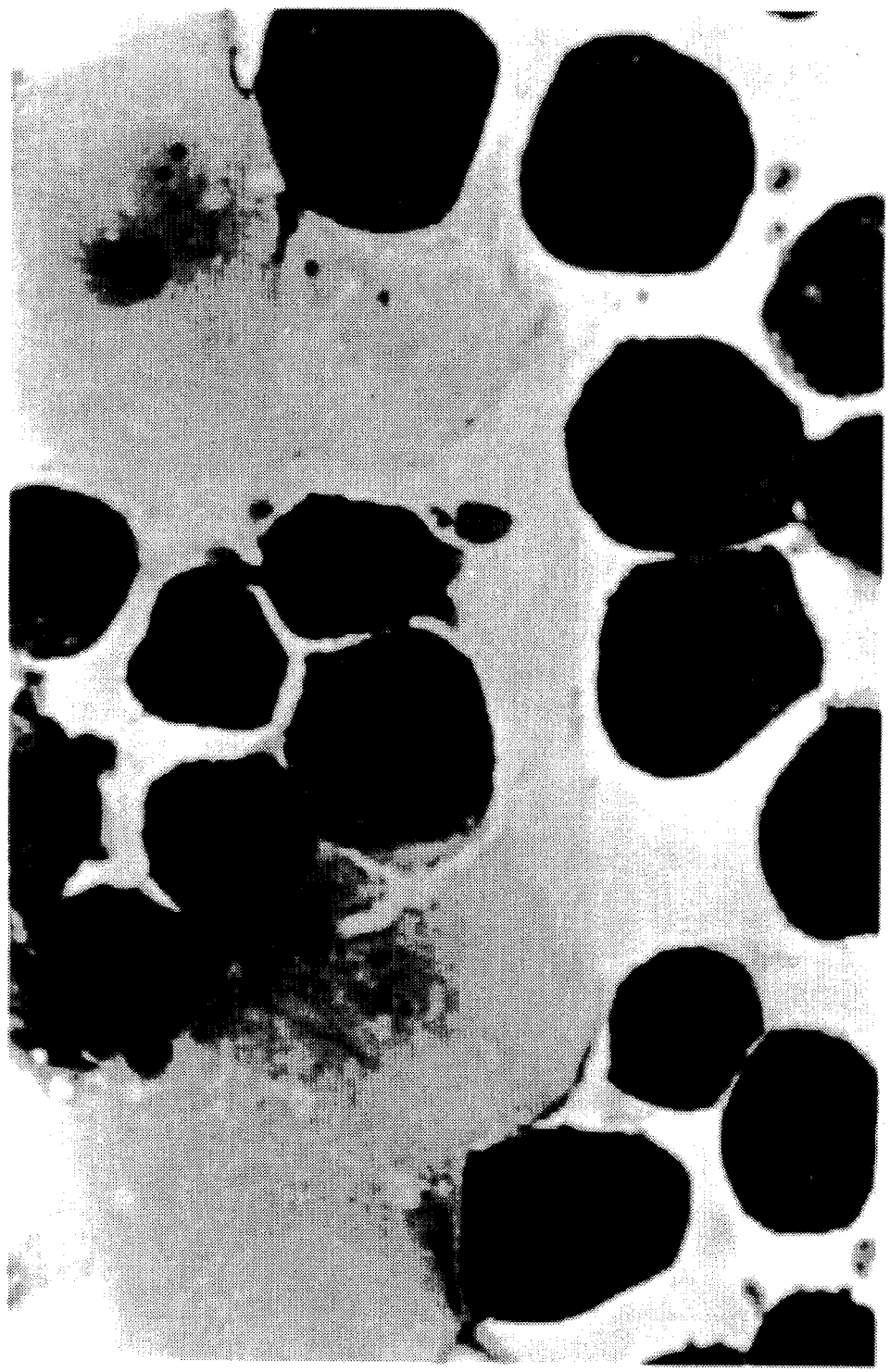

FIGS. 11A and 11B. FIG. 11A. Area plot depicting relative percentages of various hepatic cells in the adherent zones of suspended nylon screen cultures.

FIG. 11B. Cytosmear of adherent zone of a liver co-culture at 40 days showing the persistence of acidophilic cells as an entity in stromal cell-associated culture.

Figure 12:

FIG. 12. Hematoxylin and eosin stained section through a nylon screen co-culture.

Figure 13A:
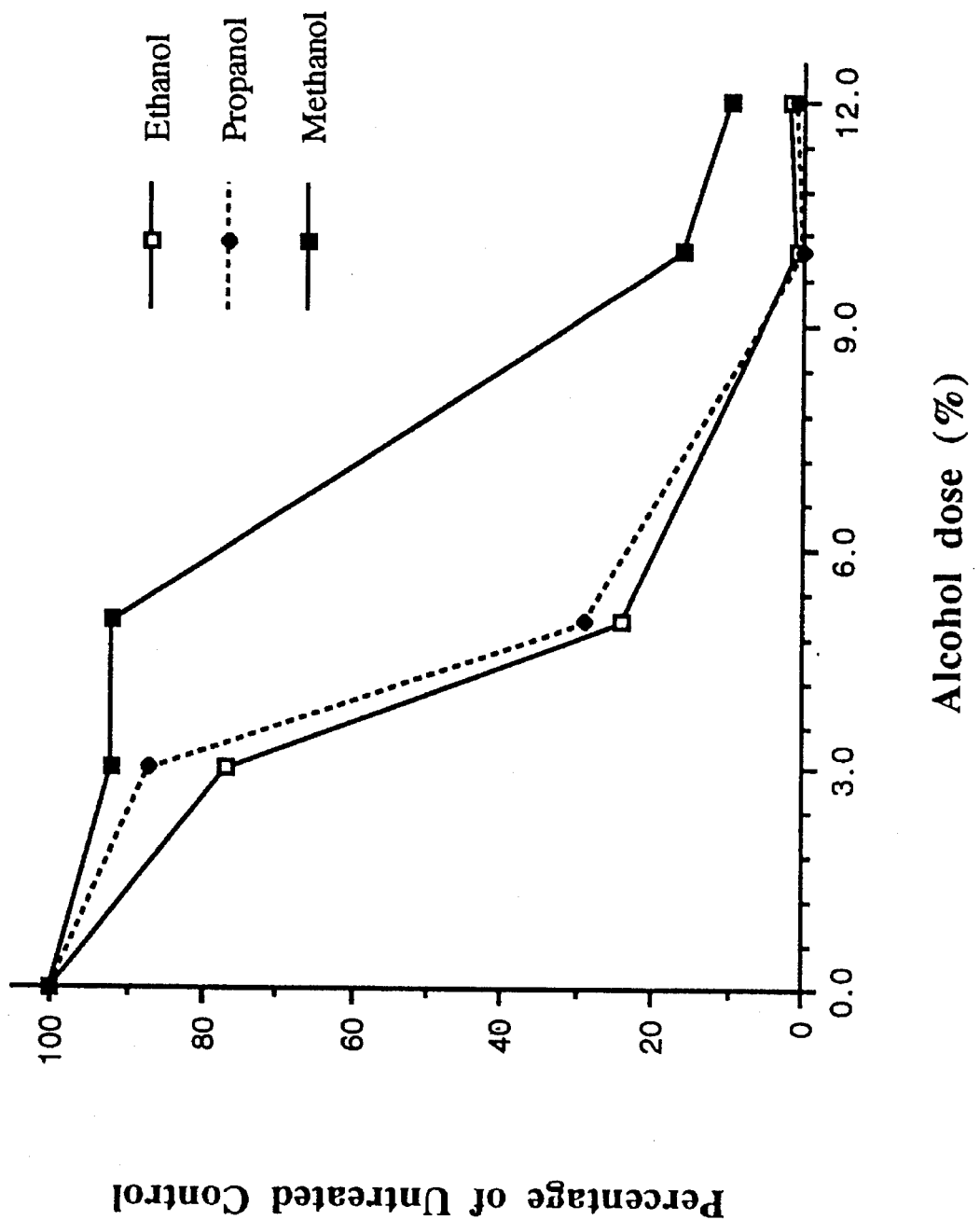
Figure 13B:
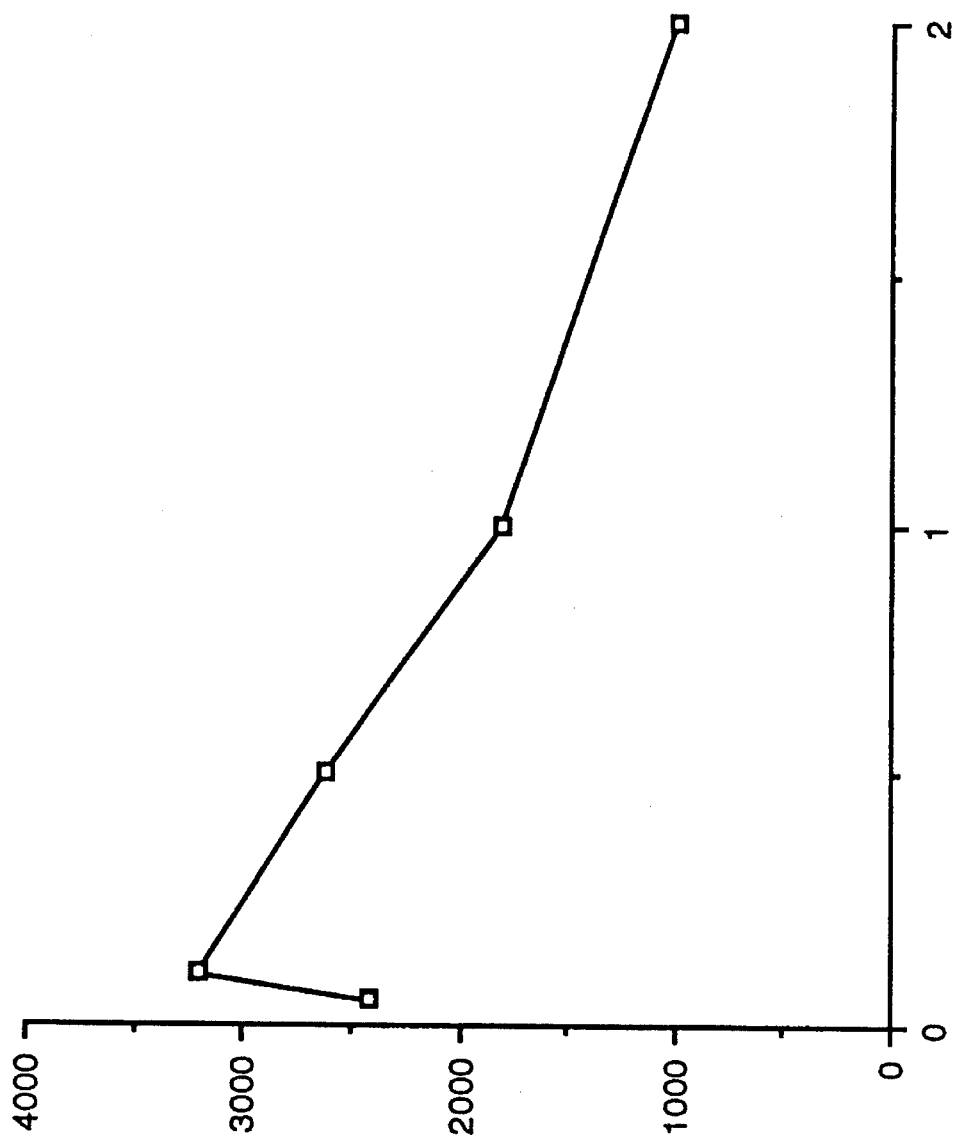
Figure 13C:
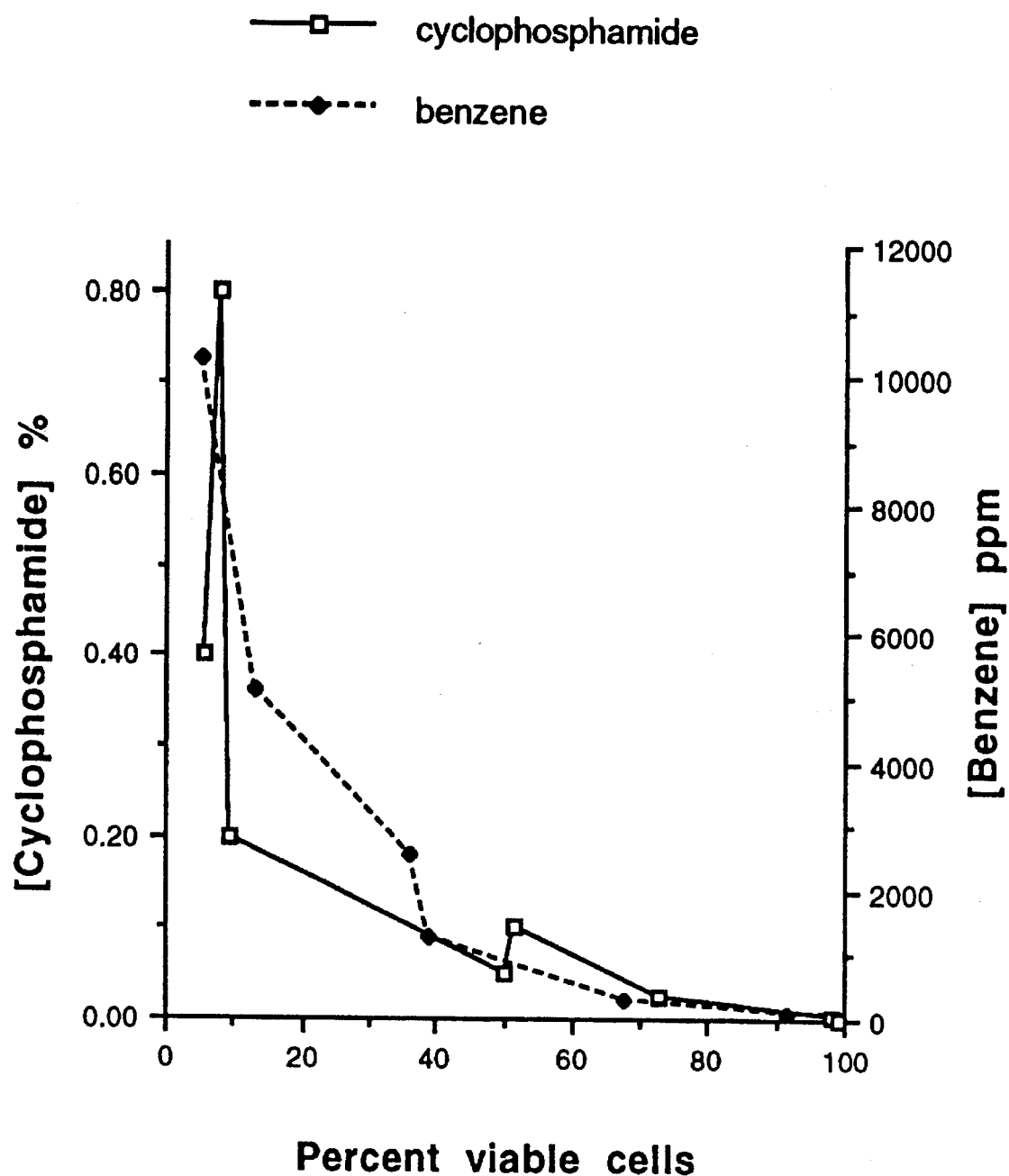

FIGS. 13A, 13B, and 13C. cultures for toxicity measurements.

FIG. 13A. Neutral viability assay showing diminished viability of co-cultured hepatocytes with increasing concentrations of alcohol.

FIG. 13B. Diminished tritiated thymidine incorporation into DNA of cultured liver cells related to a dose of 5-Fluorouracil.

FIG. 13C. Activation of cyclophosphamide and benzene by liver cells co-cultured with bone marrow cells. Under these conditions, bone marrow viability (MTT assay) diminishes with increasing doses of cyclophosphamide and benzene.

5. DETAILED DESCRIPTION OF THE INVENTION

The present invention relates to liver reserve cells, to methods of isolating and culturing these cells, and to methods of using the same.

Liver reserve cells are separated from other rat liver PC by differential gradient centrifugation, and they exhibit unique phenotypic characteristics as follows. The reserve cells are larger than all typical PC with a low nuclear size to cytoplasmic size ratio, and have two to three prominent nucleoli per nucleus. These cells primarily take up the acid component of a combination of acidic/basic stain, while other PC are strongly basophilic. Liver reserve cells have a high rate of proliferation (a doubling time of 24–28 hours) in monolayer culture and persist for even longer periods in nylon screen co-cultures with stromal cells. In culture, they are rapidly and firmly adherent to plastic as well as to other "mature" PC. Further, they are capable of differentiating into cells with typical PC morphology and function. After a rapid growth period in monolayer culture, cells apparently derive from the adherent acidophilic reserve cell culture and become detached from other cells; these have a higher nuclear to cytoplasmic size ratio and accumulate the basic component of the stain. The liver-specific functional activities of these cells include the secretion of albumin and the expression of inducible cytochrome P-450 enzymes.

The invention is discussed in more detail in the subsections below, solely for purposes of description and not by way of limitation. For clarity of discussion, the specific procedures and methods described herein are exemplified using rat liver preparations, but they are merely illustrative for the practice of the invention. Analogous procedures and techniques are equally applicable to all mammalian species, including human subjects. In fact, human liver reserve cells have been isolated from human liver preparations, following similar procedures and shown to display a phenotype consistent with the rat acidophilic liver reserve cells illustrated herein.

5.1. ISOLATION OF LIVER RESERVE CELLS

The present invention relates to liver reserve cells which are present in low numbers in a normal liver, occupying 2–5% of the total liver PC population. The larger size of these cells serves as a convenient basis for their separation from other liver cells. Thus, these cells may be isolated from a liver by differential density gradient centrifugation as described in Section 6.1.1., infra. The large cells obtained at the upper portion of the interface zone following Percoll discontinuous gradient centrifugation consists of greater than 90% large acidophilic liver reserve cells. This level of enrichment is generally acceptable for the various uses of these cells described in Section 5.4., infra.

Alternatively, liver reserve cells may be isolated by subjecting liver cell preparations to lectin chromatography, affinity chromatography involving positive and negative selection, repetitive density gradient centrifugation, or a combination thereof. For example, liver reserve cells obtained in Section 6.1.1., infra, may be negatively selected by panning using antibodies to remove fibroblasts, endothelial cells, Kupffer cells and adipocytes. Examples of such antibodies include anti-MHC class II antigens and anti-vW factor VIII specific for Kupffer cells and endothelial cells, respectively. These antibodies may be applied in any combination repeatedly or in a sequential manner. Upon binding to the antibodies, the cells may be removed by adsorption to a solid surface or column coated with a second step antibody; i.e., an anti-mouse antibody, if the primary antibody is of mouse origin; or if the antibodies are conjugated with biotin, the antibody-bound cells can be removed by an avidin-coated column; or if the antibodies are conjugated to magnetic beads, the cells expressing antigens recognized by the antibodies can be removed in a magnetic field. A similar procedure may be followed for positive selection, except that antibodies directed to liver reserve cell-specific surface markers are utilized to sort out the desired cell population.

5.2. LONG-TERM CULTURE OF LIVER RESERVE CELLS AND OTHER PARENCHYMAL CELLS

Liver, although a mitotically quiescent organ, has the potential to regenerate after total hepatectomy or partial chemical destruction (Bucher, 1963, Int. Rev. Cytol. 15:245–300; Naughton et al., 1977, Science 196:301–302). That this phenomenon may be related to liver reserve cells is important in the understanding of the induction of both hepatic regeneration and hepatocarcinogenesis. In a specific embodiment by way of example in Example 6, infra, liver PC or acidophilic liver reserve cells are shown to grow on nylon screen seeded with stromal cells and persist for extended periods of time in culture. Additionally, the presence of stromal cells or the matrix proteins secreted by these elements is necessary for the prolongation of hepatocyte cytochrome P-450 enzyme function (Deschenes et al., 1980, In Vitro 16:722–730; Michalopoulos and Pitot, 1975, Exp. Cell Res. 94:70–78; Reid et al., 1980, Ann. N.Y. Acad. Sci. 349:70–76; Bissell et al., 1987, J. Clin. Invest. 79:801–812; Dunn et al., 1989, FASEB J. 3:174–177; Guguen-Guilluozo, et al., 1983, Exp. Cell Res. 143:47–54; Begue et al., 1983, Biochem. Pharmacol. 32:1643–1646; Kuri-Harcuch and Mendoza-Figueroa, 1989, Differentiation 41:148–157). Fibronectin, laminin, and collagen are produced by the hepatic stromal cells onto which the PC or liver reserve cells can be seeded. The levels of these substances, as estimated by the fluoresence intensity after labelling with primary antibodies and fluorochrome-conjugated secondary antibodies are higher than that observed in liver organ slices. The increased synthesis of these extracellular matrix proteins mimics their expression pattern in fetal tissues.

Extracellular matrix substances produced by stromal cells in the liver co-cultures may influence cell division and gene expression in PC and liver reserve cells (Tonomura et al., 1987, J. Cell Physiol. 130:221–227; Sudhakaran et al., 1986, Exp. Cell Res. 167:505–516). In this regard, DNA synthesis rates for hepatocytes in vitro are higher on fibronectin vs. laminin-rich substrates (Tonomura et al., 1987, J. Cell Physiol. 130:221–227) and the synthesis of α-fetoprotein and albumin by cultured liver cells is greatest in association with type IV collagen (Sudhakaran et al., 1986, Exp. Cell Res. 167:505–516). Similar to the liver in vivo, the extracellular matrix of hepatocyte co-cultures of the present invention contains fibronectin, laminin, and collagen IV. Production of TGFβ, fibrinogen and other liver-specific proteins by the cultured hepatocytes is also observed.

When the large acidophilic liver reserve cells are placed in a long-term co-culture with stromal cells, three populations of cells emerge during the course of culture. The majority of the cultured cells display a typical PC morphology. While a substantial number of the remaining cells are stromal cells, a small yet detectable population of acidophilic reserve cells is invariably present over the course of several weeks. The ability to maintain these hepatic cells long-term, even in a quiescent state, is important for assessing the effects of various toxicants on these cells (Michalopoulos and Pitot, 1975, Exp. Cell Res. 94:70–78; Bissell et al., 1987, J. Clin. Invest. 79:801–812; Guguen-Guilluozo et al., 1983, Exp. Cell Res. 143:47–54). In the co-culture system, cytochrome P-450 enzyme activity is evident in rat hepatocytes for more than 60 days of culture. This activity is observed in all distinct populations of cells based on FLS vs. SS characteristics. The smaller cells in these mixed cultures, which display low to moderate granularity, appear to be endothelial and Kupffer cells. Both endothelial and Kupffer cells have been reported to modulate PC cytochrome P-450 activity in vivo and in vitro (Begue et al., 1983, Biochem. Pharmacol. 32:1643–1646; Ratanasavahn et al., 1988, Xenobiotica 18:765). Macrophages have also been reported to exhibit their own detoxifying activities (Wichramasinghe, 1987, Clin. Lab. Hematol. 9:271–280.). In this regard, it was reported recently that the macrophage component of bone marrow stroma was capable of metabolizing EFEE to fluorescein (Naughton et al., 1992, Proc. Soc. Exp. Biol. Med. 201:481–490). However, the Kupffer cells in the co-culture system are considerably smaller in size than most of the PC, and it is primarily the larger cells that display the greatest cytochrome P-450 activity as manifested by their ability to metabolize fluorescein to EFEE.

The growth of long-term cultured liver PC or liver reserve cells may be enhanced by the addition of various supplements in the culture media. Tissues that normally contain low levels of iron exhibit toxic responses to iron at higher levels, but hepatocytes normally subsist in an iron-rich environment and their intracellular iron stores rapidly diminish in vitro. Thus, the failure of hepatic cells to proliferate in most cultures may be attributed in part to a deficit in iron. Supplementation of the culture medium with iron salts and saturated transferrin inhibits albumin production but enhances radiothymidine incorporation into hepatocytes. Mammalian iron storage occurs primarily in the liver and spleen. This mineral is necessary for cell growth,, in part because of its role as a co-factor in the activation of ribonucleotide reductase which is needed for DNA synthesis (Reichard and Ehrenbergen, 1983, Science 221:514–519). In addition, the number of transferrin receptors has been correlated with proliferative activity (Sutherland et al., 1981, Proc. Nat. Acad. Sci. USA 78:4515–4519); these vary during the cell cycle with highest expression occurring in S phase (Yeh et al., 1982, Exp. Cell Res. 138:429–434). Monoclonal antibody 42/6, which recognizes the transferrin receptor, blocks transferrin binding and inhibits the growth of several cell lines in vitro (Trowbridge et al., 1984, Biochem. Pharmacol. 33:925–932; Mendelsohn et al., 1983, Blood 62:821–826).

Hepatic eythropoietic factor (HEF), a factor found in the sera of animals with livers regenerating after partial hepatectomy (Naughton et al., 1980, Amer. J. Physiol. 238:E245–E252), also enhances DNA synthesis of hepatocytes in the culture system described herein. There have been reports on the trophic effects of sera from hepatectomized animals on liver and other tissues of normal animals as well as cultured hepatic cells (Bucher, 1963, Int. Rev. Cytol. 15:245–300). Although the precise mechanisms controlling hepatic regeneration have not been elucidated fully, hepatotropic activity was found in the effluent of regenerating liver that was perfused ex situ (Dornfest et al., 1981, Ann. Clin. Lab. Sci. 11:27–46), suggesting that the liver may contribute to its own regulation. Currently, these factors have not been fully characterized but may all be useful in supporting long-term growth of liver reserve cells and PC.

5.3. CHARACTERIZATION OF LIVER RESERVE CELLS

As shown by Example 6, infra, liver reserve cells can be isolated and enriched by various procedures. Liver reserve cells have distinct physical characteristics that distinguish them from oval cells or any other hepatocytes reported thus far. For example, they are larger ($\geq 30$ μm in diameter) than typical hepatic PC which are generally in the range of 22–26 μm in diameter, have a low nuclear:cytoplasmic ratio and have 1 or 2 nuclei, each of which has 2–3 prominent nucleoli. When stained with a combination of acidic and basic stains such as Diff-Quick, they primarily retain the acid component of the stain. In fact, since all liver PC are highly basophilic, the liver reserve cells are stained so faintly that they were originally thought to be "cell ghosts" or dead cells. In order to visualize these cells more clearly, a cytosmear is usually stained for longer periods of time to enhance their uptake of the stain. Thus, the term "acidophilic" is used in comparison to other liver cell populations which are highly basophilic. In addition, unlike oval cells, they are present in normal liver, do not require prior induction with chemical carcinogens, and they either express and/or develop into cells which display the PC-associated functions of albumin secretion and cytochrome P-450 enzyme activity. In culture, they are strongly adherent to plastic and can also adhere to other hepatic PC. They have a relatively high mitotic index, capable of dividing every 24 to 28 hours regularly for ten days to two weeks in monolayer culture, and after this period become non-adherent. At this stage, the detached cells are morphologically indistinguishable from the typical hepatic PC.

Liver reserve cells may be characterized further by their reactivity with a variety of known cell surface marker-specific monoclonal antibodies. For example, they express low levels of MHC Class I antigen, but do not express detectable MHC Class II antigen. In addition, liver reserve cells may express other markers which have not yet been identified. Therefore, in order to further characterize these cells, they may be used to generate antibodies against their cell surface molecules.

Also within the scope of the invention is the production of polyclonal and monoclonal antibodies which recognize novel antigenic markers expressed by liver reserve cells. Such antibodies may have a variety of uses such as the isolation of liver reserve cells by affinity chromatography. Various procedures known in the art may be used for the production of antibodies to liver reserve cells. Various host animals can be immunized by injection with viable liver reserve cells, fixed cells or membrane preparations, including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peotides, oil emulsions, keyhole limpet hemocyanin, dinitrophenol, and potentially useful human adjuvants such as BCG (bacille Calmette-Guerin) and *Corynebacterium parvum*.

Monoclonal antibodies to novel antigens on liver reserve cells may be prepared by using any technique which provides for the production of antibody molecules by continuous cell lines in culture. These include, but are not limited to, the hybridoma technique originally described by Kohler and Milstein (1975, Nature 256, 495–497), and the more recent human B-cell hybridoma technique (Kosbor et al., 1983, Immunology Today 4:72; Cote et al., 1983, Proc. Natl. Acad. Sci. 80:2026–2030) and the EBV-hybridoma technique (Cole et al., 1985, Monoclonal Antibodies and Cancer Therapy, Alan R. Liss, Inc., pp. 77–96). Techniques developed for the production of "chimeric antibodies" by splicing the genes from a mouse antibody molecule of appropriate antigen specificity together with genes from a human antibody molecule can be used (e.g., Morrison et al., 1984, Proc. Natl. Acad. Sci., 81:6851–6855; Neuberger et al., 1984, Nature, 312:604–608; Takeda et al., 1985, Nature 314:452–454). In addition, techinques described for the production of single chain antibodies (U.S. Pat. No. 4,946,778) can be adapted to produce single chain antibodies.

Syngeneic, allogeneic, and xenogeneic hosts may be used for injection of liver reserve cells prepared in viable form, or in fixed form, or as extracted membrane preparations thereof. Monoclonal antibodies can be screened differentially by selective binding to liver reserve cells, but not to other liver PC and stromal cells.

Antibody fragments which contain the binding site of the molecule may be generated by known techniques. For example, such fragments include but are not limited to, the $F(ab')_2$ fragments which can be produced by pepsin digestion of the antibody molecule and the Fab fragments which can be generated by reducing the disulfide bridges of the $F(ab')_2$ fragments.

5.4. USES OF LIVER RESERVE CELLS

The ability of the large acidophilic cells to proliferate and differentiate into mature biologically active hepatocytes in culture indicates that they are the reserve cells of the liver. As such, they may be particularly useful in transplantation therapy to replace and/or reconstitute a liver that is genetically deficient, infected by an infectious agent and/or partially destroyed.

A major impediment in the current attempts to achieve stable integration of foreign genes in eukaryotic host cells of different organs is the inability of most of these cells to proliferate in vitro. This is particularly problematic for attempts to insert exogenous genes in liver cells, since hepatocytes do not normally undergo cell division in vitro. Recently, gene transfer studies were performed using hepatocytes isolated from Watanabe heritable hyperlipidemic rabbits, which are widely used as an animal model for familial hypercholesterolemia in humans. Like their human counterparts, the Watanabe rabbit cells contain a genetic deficiency in low density lipoprotein (LDL) receptor, leading to high levels of cholesterol in the circulation and increased incidence of premature coronary artery disease (Wilson et al., 1990, Proc. Natl. Acad. Sci. USA 87:8437). Rabbit hepatocytes were infected with recombinant viruses carrying a functional LDL receptor gene, and shown to cause a temporary amelioration of hyperlipidemia in the genetically deficient rabbits following transplantation. It is believed that the success rate of this form of therapy can be further augmented if the gene of interest can achieve more stable integration into a population of recipient cells, which is capable of substantial cell division. Since the liver reserve cells proliferate in vitro, especially for longer time periods in the co-culture system described herein, these cells may be ideal candidates as recipients for the introduction of exogenous genes in culture.

A variety of inborn errors of metabolism are caused by inherited genetic deficiency in liver cells. These diseases may be treated by transplantation of liver reserve cells carrying functional copies of the correct genes. In brief, this procedure involves isolation of liver reserve cells from patients afflicted with a particular deficiency, transfer of functional genes into these cells to correct the genetic defect by conventional gene transfer technologies, confirmation of stable integration and expression of the desired gene products, and transplantation of the cells into the patients' own livers for reconstitution. This approach is particularly applicable in situations where a single gene defect is responsible for the disease and the defective gene has been identified and molecularly cloned; however, it is not limited only to these conditions. In addition to gene therapy in an autologous setting, liver reserve cells carrying functional genes may also be transplanted into allogeneic HLA-matched individuals. Examples of target genes and their related liver diseases that are amenable to this form of therapy include, but are not limited to, the LDL receptor gene in familial hypercholesterolemia, the clotting factor genes for factors VIII and IX in hemophilia, the alpha 1-antitrypsin gene in emphysema, the phenylalanine hydroxylase gene in phenylketonuria, the ornithine transcarbamylase gene in hyperammonemia, and complement protein genes in various forms of complement deficiencies.

The liver is a center of production for many secretory proteins. It is anatomically connected with the circulatory system in such a way that allows a efficient release of various proteins into the bloodstream. Therefore, genes encoding proteins that have systemic effects may be inserted into liver reserve cells as opposed to the specific cell types that normally produce them, especially if it is difficult to integrate genes into these cells. For example, a variety of hormone genes or specific antibody genes may be inserted into liver reserve cells for the secretion of their gene products into the circulation.

For the practice of the invention, liver reserve cells isolated by the procedures described in Example 6, infra, are used as recipients in gene transfer experiments. The cells may be grown optimally in a co-culture system with stromal cells prior to, during, and after introduction of an exogenous gene. The proliferative activity of these cells may be enhanced by various iron supplements described in Section 5.2., supra, and in vitro differentiation of these cells may be minimized by the addition of cytokines in a manner similar to the use of leukemia inhibitory factor in hematopoietic stem cell cultures.

For the introduction of exogenous genes into the cultured reserve cells, any cloned gene may be transferred using conventional techniques, including, but not limited to, microinjection, transfection and transduction. In addition, if the liver reserve cells express receptors for the asialoglycoprotein, plasmids containing the genes of interest may be conjugated to asialoglycoprotein and added to cells to induce uptake and expression (Wu et al., 1991, J. Biol. Chem. 266:14338). This procedure is more gentle on the recipient cells.

The preferred method of gene transfer utilizes recombinant viruses, such as retroviruses and adenoviruses. For example, when using adenovirus expression vectors, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing the gene product in infected liver reserve cells (e.g., see Logan & Shenk, 1984, Proc. Natl. Acad. Sci. USA 81:3655–3659). Alternatively, the vaccinia virus 7.5K promoter may be used. (e.g., see, Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931). Of particular interest are vectors based on bovine papilloma virus which have the ability to replicate as extrachromosomal elements (Sarver, et al., 1981, Mol. Cell. Biol. 1:486). Shortly after entry of this DNA into cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of any gene of interest in liver reserve cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, liver reserve cells can be transformed with a cDNA controlled by appropriate expression control elements (e.g., promoter, enhancer, sequences, transcription terminators, polyadenylation sites, etc..), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered liver cells may be allowed to grow for 1–2 days in an enriched media, and then are switched to a selective media. A number of selection systems may be used, including but not limited to the herpes simplex virus thymidine kinase (Wigler, et al., 1977, Cell 11:223), hypoxanthineguanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes. Also, antimetabolite resistance can be used as the basis of selection for dhfr, which confers resistance to methotrexate (Wigler, et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072; neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

The liver reserve cells that have integrated a particular gene as measured by their expression of its gene product by techniques such as Northern blots and ELISA, may be transplanted into the patients from whom the cells are originally derived or into a HLA-matched individual. For HLA-matched allogeneic transplantation, the liver reserve cells may not necessarily require gene transfer prior to transplantation. For instance, liver reserve cells obtained from a donor who possesses a functional gene encoding clotting factor VIII may be used directly by transplantation into a HLA-matched hemophiliac patient. The transplanted cells will presumably multiply and give rise to mature PC performing normal liver functions, including the production of clotting factor VIII.

In addition to using liver reserve cells for correcting liver gene defects, these cells may be used to replenish the liver parenchyma in the case of hepatic cirhosis, or they may be engineered against liver specific infectious diseases. For example, uninfected liver reserve cells may be obtained from an early stage hepatitis patient and used as recipients for genes encoding anti-sense RNA that is complementary to critical replication-related genetic elements of a hepatitis virus. The cells may then be transplanted into the patients to control spread of the virus and restore normal liver function.

6. EXAMPLE: IDENTIFICATION, ISOLATION AND CHARACTERIZATION OF LIVER RESERVE CELLS IN LONG-TERM LIVER CULTURES

6.1. MATERIALS AND METHODS

6.1.1. CELL ISOLATION

Cells were produced from male Long-Evans rats at 6–9 weeks of age following sodium pentobarbital anesthesia. An 20 gauge angiocath (Terumo Corp., Japan) was inserted into the hepatic portal vein and secured with two 4-0 ligatures. The liver was perfused with 500 ml of $Ca^{++}$-free buffer (Pertoft and Smedsrod, 1987, In: Cell Separation: Methods and Selected Applications, Vol. 4, T. G. Pretlow II and T. P. Pretlow, editors, Academic Press, New York, pp 1–24) which was delivered at 50 ml/min by a Harvard Instruments (MA) peristalic pump and gently massaged until uniformly blanched. The liver was placed on a modified Buchner funnel and perfused with a buffer containing $Ca^{++}$ and 0.05 g/dl type IV collagenase (Sigma Chemical Co, MO) in a recirculating system for 15–20 min. The liver was then transferred to a Petri dish containing collagenase buffer supplemented with 1.5% bovine serum albumin (BSA) and the hepatocytes were liberated into suspension after the perforation of Glisson's capsule, filtered through a 185 µm nylon sieve, pelleted by centifrifugation, and resuspended in complete medium, DMEM conditioned with 6% FBS and 10% equine serum and supplemented with 35 µl glucagon (Sigma #G9261), 10 µg insulin (Sigma #14011), 0.25 g glucose, and 250 µl hydrocortisone hemisuccinate per 500 ml of medium.

Hepatic cells were separated into the following subpopulations using Percoll gradient centrifugation:

Parenchymal cells. Cell suspensions were layered atop a solution of 25% Percoll (Pharmacia Inc., NJ) in 10X Dulbecco's phosphate buffered saline (PBS) and spun at 800×g (10° C.) for 10 min. to remove subcellular debris. Cells were washed, resuspended in medium, and centrifuged against a 70% Percoll gradient. The pellet of this preparation contains a relatively pure population ($\geq$90%) of hepatic PC. The osmolality of this suspension was calculated to be 290 mOs using the method of Timonen and Saksela (Timonen and Saksela, 1980, J. Immunol. Methods 36:285).

Liver reserve cells. A population of large ($\leq$30 µm in diameter), acidophilic cells which proliferate and differentiate in culture to cells resembling mature hepatocytes was separated as follows: single cell suspensions of freshly isolated liver cells were centrifuged (500×g/5 min) and the pellet was resuspended in medium. The cell suspension was layered over 25 ml of a 70% v/v solution of 'neat' Percoll and 1X PBS (Sigma Chemical Co., MO) and centrifuged at 800×g for 10 min. The two lower zones (of 4) were pooled, washed, and centrifuged against 25%/50% (v/v/, neat Percoll/1X PBS) discontinuous gradient yielding a distinct interface zone and a pellet. The interface (density= 1.0381 g/ml) consists of about 90% large, lightly acidophilic, mono- or binuclear cells with multiple, prominent nucleoli.

Stromal cells. Hepatic fibroblasts, endothelia, and Kupffer cells were concentrated in the following manner: freshly isolated liver cells were centrifuged against a 70% Percoll (Pharmacia) gradient in 10X PBS (density=1.09 g/ml) for 10 min. forming a pellet and a central zone. Cells from the central zone were washed and centrifuged on a 25%/50% Percoll column. The interface zone (density=1.03625 g/ml) contained fibroblastic cells, macrophages, endothelial cells, and occasional peripheral blood leukocytes.

6.1.2. NYLON SCREEN CULTURE 15 mm×60 mm nylon filtration screens (Tetko, NY) with 210 µm spaces were treated with 1.0M acetic acid, washed in distilled water, and soaked in fetal bovine serum (FBS) to enhance cellular attachment. These were placed in Tissue Tek slide chambers (Nunc, Inc., IL) and inoculated with $10^7$ liver stromal cells which were lifted enzymatically from monolayer culture. Screens were transferred to 25 cm² flasks 18–24 hr later. Within 2 weeks, projections of developing stromal cells extended across 3 to 4 out of every 5 mesh openings. Screen cultures were placed in slide chambers, inoculated with 2–5×10⁶ hepatic PC or acidophilic liver reserve cells, and transferred to 25 cm² flasks after 18–24 hr. Cells were cultured (5% $CO_2$/35°–37° C./>90% humidity) in complete medium. Complete medium replacement was performed 6 times per week. Experimental supplements to the medium included saturated transferrin, ferrous sulfate, ferric citrate, and sera from rats with regenerating livers. The latter has been found to contain a factor(s) that induces hepatocyte proliferation (Bucher, 1963, Int. Rev. Cytol. 15:245–300; Naughton et al., 1980, Amer. J. Physiol. 238:E245–E252).

6.1.3. ALBUMIN ASSAY

Medium was collected during each feeding and tested for the presence of rat albumin using the enzyme-linked immunosorbent assay (ELISA) (Bissell et al., 1987, J. Clin. Invest. 79:801–812). The chromatographically pure rat albumin and peroxidase-conjugated sheep anti-rat albumin antibody were purchased from Cappel Inc (PA), and absorbance at 490 nm was determined using a kinetic microplate reader (Molecular Devices Inc, CA). 100 µl of spend medium was added to 96 well plates and stored at 0° C. for 12–14 hr. The wells were washed with 0.5% Tween-20 in PBS and non-specific binding sites were blocked with 5.0% BSA in PBS. After washing with 0.5% Tween-20, 100 µl of sheep anti-rat albumin-peroxidase conjugate was added to each well and incubated for 1 hr at 22° C.). The wells were washed with 0.5% Tween-20 and incubated for 15 min with o-phenylenediamine substrate (Cappel Inc., PA). The reaction was stopped and absorbance was measured on an EIA reader. Results were read from a standard curve.

6.1.4. CELL COUNTS

Total non-adherent and adherent zone cell counts were determined using an impedance principle cell counter (Counter Electronics, FL). Differential cell counts were based strictly on the morphology of cells stained using Diff-Quick (Baxter SP, IL). Diff-Quick Stain Set consists of three solutions: (1) The Fixative Solution contains 1.8 mg/L Triarylmethane Dye and 100% PDC in methyl alcohol; (2) Solution I contains 1 g/L Eosin Y, an anion dye, 100% PDC, buffer and 0.01% sodium azide as preservative; and (3) Solution II contains 1.25 g/L Thiazine Dye Mixture, 100% PDC (0.625 g/L Azure A and 0.625 g/L Methylene Blue) and buffer. The cytosmear slide was dipped in Fixative Solution five times, followed by Solution I five times and Solution II five times. Thereafter, the slide was rinsed with distilled or deionized water and allowed to dry prior to examination under the microscope. Cells were scored as parenchymal versus stromal. Phagocytosis of colloidal carbon and reaction with FITC-conjugated antibodies to the vW factor VIII segment were used to identify Kupffer cells and endothelial cells, respectively.

6.1.5. FLOW CYTOMETRY

Phenotypic Analysis. Cells derived from liver cultures were reacted on ice with 100 µl mouse monoclonal $IgG_1$ polymorphic antibodies to either rat MHC I or MHC II antigens which were conjugated to fluorescein isothiocyanate (FITC) (Serotec Inc, UK). Control cells were treated with mouse $IgG_1$-FITC alone. The samples were analyzed using an EPICS C flow cytometer (Coulter Electronics, Hialeah, Fla.) tuned to a wavelength of 488 nm with the fluorescence gain adjusted to exclude $\geq$98% of the control cells. Windows were established around the various cell populations using the forward light scatter (FLS) vs. side scatter (SS) two parameter histogram and the percentage of positively fluorescent events was determined.

Cytochrome P-450 assay. Freshly isolated hepatocytes, hepatocytes 24 hr after isolation, and hepatocytes derived from suspended nylon screen cultures of various durations were assayed for cytochrome P-450 monooxygenase activity by flow cytometry. One nM of a 1 µM stock solution of 2,3,7,8-tetrachlorodibenzo-p-dioxin (TCDD) (Chemical Carcinogen Repository, National Cancer Institute, Kansas City, Mo.) in dimethylsulfoxide (DMSO) (Sigma Chem. Co.) was added to cell cultures for 18 hr to induce enzyme activity (Miller, 1983, Anal. Chem. 133:46–57). This non-fluorescent compound was found to be an ideal inducer for this assay. Cells in suspended nylon screen cultures were lifted using a trypsin-collagenase mixture (Naughton and Naughton, 1989, Ann. N.Y. Acad. Sci. 554:125–140), pelleted and resuspended in phosphate buffered saline (PBS) at a density of ~5×10$^5$ cells/ml, stored on ice for 1 hr, and gradually warmed to 37° C. Cells were analyzed for evidence to cytochrome P-450 enzyme activity by quantifying incremental fluorescence in cells accumulating ethoxyfluorescein ethyl ester (EFEE) (Miller, 1983, Anal. Chem. 133:46–57; White et al., 1987, Biochem. J. 247:23–28). Cells were incubated with 50 nM EFEE (Molecular Probes, Eugene, Oreg.) in PBS for 5 min at 37° C. and examined for green fluorescence on a flow cytometer with a 515 nm long-pass filter and tuned to the 488 nm band. Fluorescence was gated on various populations of cells based on differences in FLS vs. SS characteristics and was measured once/minute for up to 15 min in samples maintained at 37° C. Fluorescein accumulation in cells over time was indicative of cytochrome P-450 activity (Miller, 1983, Anal. Chem. 13:46–57; White et al., 1987, Biochem. J. 247:23–28).

Cell cycle analysis. Cells dissociated from the adherent zones of suspended nylon screen liver cell cultures were subjected to morphometric analysis to ascertain the relative percentages of cells at different stages of the cell cycle. Cells were stained for DNA content using a modification of the method of Fried et al (Fried et al., 1978, J. Histochem. Cytochem. 26:921–933) and Taylor (Taylor, 1980, J. Histochem. Cytochem. 28:1021–1024). A staining solution consisting of 0.05 mg/ml of propidium iodide (Sigma Chem. Co., St. Louis, Mo.) in distilled water with 1.5% Triton-X-100 at a 1 to 5 (v/v) ratio with complete medium was added and the tubes were gently agitated using an orbital shaker for 2–3 min. RNase (1 mg/ml, 50–75 Kunitz units/ml) (Sigma Chem. Co.) was added to each tube for 3 min. Suspensions were filtered through a 50 µm nylon screen. After gating on forward light scatter to eliminate debris from the histogram, red fluorescence was measured on log scale using the cytofluorograph. Histograms were saved to List Mode and analyzed using the PARA I program (Coulter Electronics, Hialeah, Fla.). The coefficient of variation (CV) of the $G_1/G_0$ peak of all samples was ≦3.0.

Statistical Analysis. Flow cytometry measurements were taken in triplicate on sample sizes of 5,000 (phenotypic analysis) to 10,000 (cell cycle analysis) events. EFEE to fluorescein conversion was measured as a function of time with 3,000 to 5,000 events being sampled per minute. All results are expressed at mean ±1 standard error of the mean (sem). Levels of significance (P) were determined using Student's T test. Data were considered significant at the 5% level.

6.1.6. IMMUNOFLUORESCENCE

Specimens were fixed in 95% ethanol (24 hr/4° C.), dehydrated in absolute ethanol under the same conditions, and cleared in xylene (8 hr/4° C.) prior to embedding in paraffin at 56° C. 7 µm sections were cleared in xylene, dehydrated in a graded series of ethanols, and predigested with a bovine testicular hyaluronidase (Sigma Chem Co., MO) solution at 0.5 mg/ml in 0.1N sodium acetateacetic acid buffer at pH=6.0 for 5 min. Slides were blocked prior to the addition of primary antisera with a solution containing 4% goat serum, 0.1% BSA, and 0.1% Tween-20 in 0.1M NaCl. Polyclonal rabbit primary antibodies to either fibronectin or laminin (Telios Pharmaceuticals, CA) were diluted 1:100 in 0.01M Tris-Cl at pH=7.6 containing 1.0% goat serum and reacted with the sections for 1–3 hr at 22° C. Slides were washed 5× with 0.1% solution of Tween-20 in 0.1M NaCl and placed in Tris buffer for 10 min prior to labelling with goat anti-rabbit IgG conjugated to R-phycoerythrin (Sigma Chem. Co., MO). Sections were counterstained with propidium iodine for 30 min, mounted with Gelmount, and studied on a Nikon Epifluorescence microscope.

6.1.7. ELECTRON MICROSCOPY

Adherent zone cells were dissociated with collagenase, washed, and placed in complete medium for 4–6 hr. Cells were then pelleted by centrifugation, fixed for 1 hr in 2.5% glutaraldehyde in 0.1M phosphate buffer (pH 7.3), washed with buffer, postfixed with osmium tetroxide, dehydrated in increasing concentrations of ethanols and propylene oxide, and embedded in Epon 812. Sections were cut on an LKB Ultramicrotome (LKB Instruments, MD), stained with 5% uranyl acetate, and poststained with 0.4% lead citrate. Sections were examined with a JOEL 100C transmission electron microscope.

6.2. RESULTS

The results described in this section are data obtained from experiments utilizing the procedures and techniques outlined in Section 6.1., supra, which relate to the isolation, characterization, culture and function of liver reserve cells. When hepatic cells were isolated following perfusion and Percoll density gradient separation, four different morphological categories of cells were observed: 1. medium-large cells which displayed at least two nuclei, prominent nucleoli, and occasional membranous "blebs." These cells adhered to plastic dishes as well as to liver stromal cells and were localized in the 70% Percoll pellet (FIG. 1); 2. small-medium cells that did not adhere to plastic but which displayed some ability to attach to stromal cells. Cells of this group which did not attach died and underwent autolysis within 2–3 days of culture. These cells were found in all separation zones but were most prominent in the overlay medium of the 25%/50% gradient; 3. dead cells of various sizes which were concentrated in the supernatant of the 70% Percoll spin, and 4. large (≧30 µm), faintly stained acidophilic cells with 1–2 nuclei and multiple, prominent nucleoli (FIG. 2). These appear at the interface of the 25%/50% (neat Percoll/1X PBS) centrifugation, and attach to either plastic dishes, nylon screen, or stromal cells. In addition, other PC attach to these cells once they are anchored. These large, acidophilic cells proliferate for up to 2 weeks in monolayer culture, detach, and become suspended in the non-adherent zone, where they are morphologically indistinguishable from freshly pelleted hepatocytes (FIG. 3). These large acidophilic cells are believed to be the liver reserve cells. These cells persisted for the entire experimental period when co-cultured with stroma. The association between PC isolated in the 70% Percoll pellet and hepatic stromal cells is seen in FIG. 4.

Hepatic stromal cells were localized to the lower band at the interface of the 25%:50% discontinuous Percoll gradient. Included in this population were Kupffer cells (identified by their ability to phagocytose colloidal carbon and express MHC II antigens), endothelial cells (which bound antibodies to vW factor VIII), fibroblastic cells, and adipocyte-like cells. These stromal cells form a matrix on the nylon screen template which was similar in some respects to that seen with liver organ slices. Fibronectin and laminin deposition were identified by indirect immunofluorescence. The fluoresence intensity of the culture matrix labelled with anti-fibronectin antibody appeared to be greater than that seen with liver organ slices implying an enhanced sythesis of this extracellular matrix substance.

The PC which were inoculated onto semi-confluent growth of stromal cells on nylon screens proliferated for 2–3 days in culture and formed clusters of 6–20 cells in areas which previously contained only 1 or 2 cells (FIG. 5A). Proliferation appeared to cease at this time although the cells remained viable. Hepatic acidophilic cells cultured on suspended nylon screen/stromal templates displayed similar early growth patterns (FIG. 5B) but this process appeared to continue until a dense zone of firmly attached parenchymal cell clusters was evident.

Certain media supplements were active on liver cells in culture. In this regard, iron supplements enhanced the percentage of hepatocytes in S phase, as evidenced by propidium iodide cytofluorographic analysis (FIG. 6). Factor(s) found in the hepatic venous sera of rats with regenerating livers after subtotal hepatectomy also enhanced DNA synthesis of hepatocytes in this mixed culture system (FIG. 7).

Acidophilic cells also attached to liver stroma but underwent a higher rate of cluster formation than other PC. $^3$H-thymidine incorporation by these cells was significantly higher than other populations of hepatocytes in culture and cells in suspended nylon screen co-cultures continued to incorporate this radionuclide for >2 months. Differential counts of enzymatically-removed adherent zone cells indicated an increase in the numbers of parenchymal-like cells with evidence of mitotic figures. Transmission electron microscopic studies revealed that pelleted adherent zone cells displayed ultrastructural characteristics similar to those seen in freshly-prepared liver cells (FIG. 8). PC which were cultured on suspended nylon screen/stromal templates remained viable and synthesized significantly greater quantities of albumin than the PC that were used to initiate the cultures (FIG. 9A and 9B).

Cells in suspended nylon screen co-cultures sustained inducible cytochrome P-450 enzyme activity for up to 60 days as indicated by their ability to transform EFEE to fluorescein (FIG. 10A and 10B). This conversion was intracellular since the fluorescence measurements were gated on discrete populations of cells identified by their FLS vs. SS characteristics. Although the three major liver cell populations displayed this activity, highest fluorescence was observed in the larger PC. Arbitrary conversion units were calculated as the product of the percent positive fluorescence and peak channel number as described by Miller et al. (Miller, 1983, Anal. Chem. 133:46–57). Peak EFEE to fluorescein conversion was higher in the various co-cultures than in either freshly isolated liver cells or one day old liquid cultures of isolated hepatocytes. Although this parameter did not appear to be contingent upon the age of the co-culture, differential rates and duration of EFEE conversion were observed in cultures of different ages. Cultured PC manifested a diminished expression (2.6%) of class I MHC antigens when compared to freshly isolated hepatic PC (4.9%). In contrast, no MHC class I antigen expression was detectable on stromal cells and MHC class II epitopes on macrophages were substantially lower than on non-cultured cells (3.5% vs. 9.6%, respectively). FIGS. 11A, 11B and 12 demonstrate the relative percentage of three major hepatic cell types in the adherent zones of long-term co-cultures initiated with highly enriched large acidophilic liver reserve cell, grown on stromal cell coated nylon screens.

Examples of an in vitro use of the liver cell cultures described above are shown in FIG. 13A, 13B, and 13C. The toxic effects of different agents are measured in the co-cultured hepatocytes.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. Isolated liver reserve cells which retain and are stained by Eosin Y dye when stained successively by a solution comprising Eosin Y dye, and then by a solution comprising both methylene blue and Azure A dyes.

2. The liver reserve cells of claim 1 which are adherent to plastic in monolayer culture.

3. The liver reserve cells of claim 2 which are adherent to other smaller liver parenchymal cells.

4. The liver reserve cells of claim 3 which have 1 or 2 nuclei, each of which contains 2 or 3 prominent nucleoli.

5. The liver reserve cells of claim 4 which have mitotic indices higher than those of other liver cells at the initiation of in vitro culture as determined by tritiated thymidine uptake.

6. The liver reserve cells of claim 5 which differentiate to give rise to cells that produce albumin and have cytochrome P-450 enzyme activity.

7. A cellular composition wherein about 90% of the cells are liver reserve cells which retain and are stained by Eosin Y dye when stained successively by a solution comprising Eosin Y dye, and then by a solution comprising both methylene blue and Azure A dyes.

8. The composition of claim 7 in which the liver reserve cells have mitotic indices higher than those of other liver cells.

9. The composition of claim 8 in which the liver reserve cells differentiate to give rise to cells that produce albumin and have cytochrome P-450 enzyme activity.

10. A method of isolating liver reserve cells comprising subjecting a mixed population of liver cells to 70% Percoll density gradient centrifugation to obtain thereby four zones, the lower two of which contain the liver reserve cells; and pooling and centrifuging the cells in the two lower zones against a 25%/50% Percoll discontinuous gradient to obtain thereby an interface zone containing cells having a bouyant density of 1.0381 g/ml.

11. The method of claim 10 further comprising harvesting the cells from the upper portion of the interface zone to obtain a population of at least 80% of liver reserve cells.

* * * * *